(12) United States Patent
Tarassenko et al.

(10) Patent No.: US 7,031,857 B2
(45) Date of Patent: Apr. 18, 2006

(54) PATIENT CONDITION DISPLAY

(75) Inventors: Lionel Tarassenko, Oxford (GB); Neil William Townsend, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 10/479,224

(22) PCT Filed: May 29, 2002

(86) PCT No.: PCT/GB02/02550

§ 371 (c)(1),
(2), (4) Date: Dec. 1, 2003

(87) PCT Pub. No.: WO02/096282

PCT Pub. Date: Dec. 5, 2002

(65) Prior Publication Data

US 2004/0148140 A1 Jul. 29, 2004

(30) Foreign Application Priority Data

May 31, 2001 (GB) .................................. 0113212

(51) Int. Cl.
*G01R 13/02* (2006.01)
(52) U.S. Cl. ........................................ 702/67; 600/301
(58) Field of Classification Search ................ 702/16, 702/19, 32, 57, 67, 70, 71, 123, 124, 146, 702/158, 180, 183, 189, 193; 706/15, 16, 706/25; 600/300, 301, 532
See application file for complete search history.

(56) References Cited

U.S. PATENT DOCUMENTS

| | | | | |
|---|---|---|---|---|
| 5,339,826 A | * | 8/1994 | Schmidt et al. | 600/544 |
| 5,419,332 A | * | 5/1995 | Sabbah et al. | 600/455 |
| 5,584,291 A | * | 12/1996 | Vapola et al. | 600/301 |
| 5,749,367 A | | 5/1998 | Gamlyn et al. | 600/509 |
| 5,800,360 A | * | 9/1998 | Kisner et al. | 600/532 |
| 6,063,028 A | * | 5/2000 | Luciano | 600/300 |
| 6,134,537 A | * | 10/2000 | Pao et al. | 706/16 |
| 6,347,310 B1 | * | 2/2002 | Passera | 706/25 |
| 6,443,889 B1 | * | 9/2002 | Groth et al. | 600/300 |

(Continued)

FOREIGN PATENT DOCUMENTS

GB    2 258 311 A    2/1993

(Continued)

OTHER PUBLICATIONS

N D Khambete et al., Movement artefact rejection in impedance pneumography using six strategically placed electrodes, Jul. 16, 1999, 2000 IOp Publishing Ltd, pp. 79-88.*

(Continued)

*Primary Examiner*—Marc S. Hoff
*Assistant Examiner*—Mohamed Charioui
(74) *Attorney, Agent, or Firm*—Nixon & Vanderhye, PC

(57) ABSTRACT

Data from a plurality of sensors representing a patient's condition, including measurement signals and also secondary parameters derived from the measurement signals, are displayed in a simple way by calculating a novelty index constituting a one-dimensional visualization space. The novelty index is based on the distance of the current data point in a multi-dimensional measurement space, whose coordinates are defined by the values of the measurement signals and secondary parameters, from a predefined normal point. This may be achieved by using a suitably trained artificial neural network to sum the distance between the current data point in the measurement space and a plurality of prototype points representing normality.

35 Claims, 22 Drawing Sheets

U.S. PATENT DOCUMENTS 6,571,227 B1 * 5/2003 Agrafiotis et al. ............ 706/15
6,647,341 B1 * 11/2003 Golub et al. .................. 702/19
6,650,779 B1 * 11/2003 Vachtesvanos et al. ..... 382/228

FOREIGN PATENT DOCUMENTS

WO 99/65386 A1 12/1999

OTHER PUBLICATIONS

Tarassenko et al, "Medical Signal Processing Using the Software Monitor", DERA/IEE Workshop Intelligent Sensor Processing, Birmingham, UK, Feb. 14, 2001; XP001189057.

Maglaveras et al; "ECG Pattern Recognition and Classification Using Non-Linear Transformations and Neural Networks: A Review"; International Journal of Medicinal Informatics, Elsevier Scientific Publishers, Shannon, IR, vol. 52, No. 1-3, Oct. 1, 1998, pp. 191-208, XP004153684.

Presedo et al; "Cycles of ECG Parameter Evolution During Ischemic Episodes"; Computers In Cardiology, Indianapolis, USA Sep 8-11, 1996, New York, NY, USA, Sep. 8, 1996, pp. 489-492, XP010205943.

Lowe, et al; "Neuroscale: Novel Topographic Feature Extraction With Radial Basis Function Networks"; Advances in Neural Information Processing System 9, Online, 1997, pp. 543-549, XP002219480.

Emdin et al; "Compact Representation of Autonomic Stimulation on Cardiorespiratory Signals by Principal Component Analysis"; Proceedings of the Computers In cardiology Conference, London, Sep. 5-8, 1993, Los Alamitos, IEEE Comp. Soc. Press, US, Sep. 5, 1993, pp. 157-160, XP100128860.

Schwenker et al; "Visualization and Analysis of Signal Averaged High Resolution Electrocardiograms Employing Cluster Anaylsis and MultiDimensional Scaling"; Computers In Cardiology, 1996 Indianapolis, IN, USA Sep. 8-11, 1996, New York, NY, USA, IEEE, US, Sep. 8, 1996, pp. 453-456, XP010205934.

Sammon; "A Nonlinear Mappling for DAT Structure Analysis"; IEEE Transactions on computer, vol. C-18, No. 5, May 1969, pp. 401409.

Tipping et al; "Shadow Targets: A Novel Algorithm for Topographic Projections by Radial Basis Functions"; Artificial Neural Networks, Jul. 7-9, 1997, Conference Publication No. 440, IEEE, 1997, pp. 7-12.

Zahlmann et al; "A Neuro-Fuzzy-Classifier for a Knowledge-Based Glaucoma Monitor"; http://www-ophtel.gsf.de/~zahlmann/aime97/htm.

Maglaveras et al., "Smart Alarming Scheme for ICU Using Neural Networks"; Computers in Cardiology 1998 IEEE; vol. 25, pp 493-496.

K-Means Clustering Algorithm; http://cne.gmu.edu/modules/dau/stat/clustgalgs/clust5$_{13}$ bdy.html ; May 2001.

Abstract—Advances in Patient Connected Monitoring; pp 1-16, Mar. 2001; XP-002219479.

Fernandez E. et al. "Detection of Abnormality in the Electrocardiogram Without Prior Knowledge by Using the Quantisation Error of a Self-Organaising Map, Testing on the European Ischaemia Database", *Medical and Biological Engineering and Computing, Peter Peregrinus, Stevenage, GB*, vol. 39, No. 3, May 2001 (2004-2005), pp. 330-337, (XP001178745).

Roberts S.J. "Extreme Values Statistics for Novelty Detection in Biomedical Data Processing", *IEEE Proceedings: Stevenage, Herts, GB*, vol. 147, No. 6, Nov. 3, 2000 (200-11-3), pp. 363-367 (XP006014529).

* cited by examiner

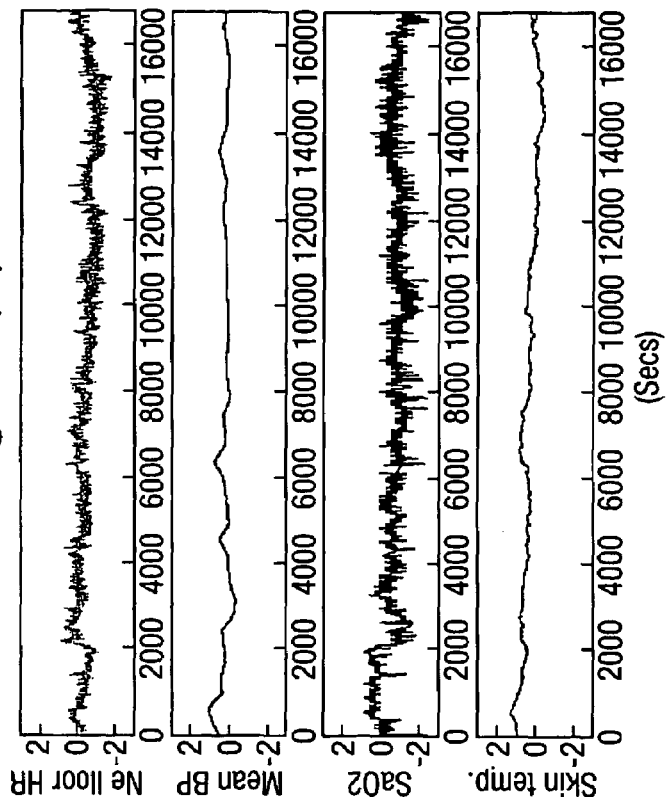
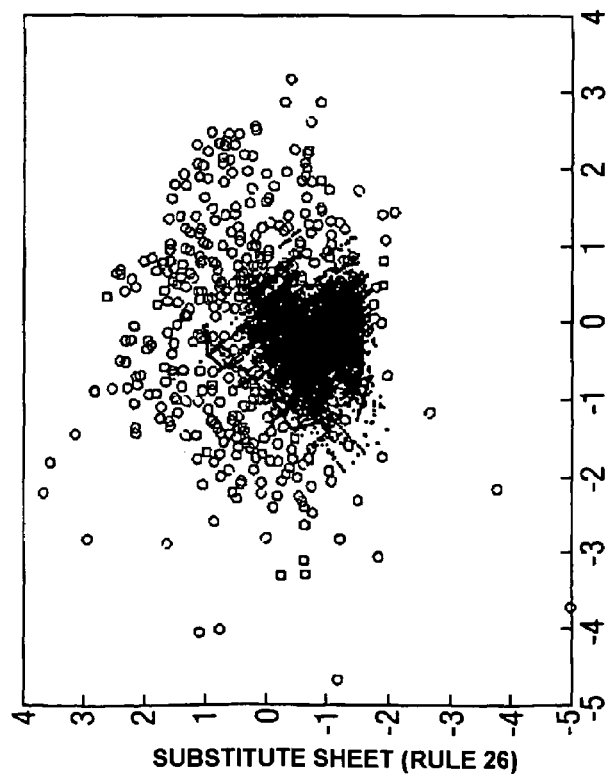
Fig.14 (B).
Fig.14 (A).

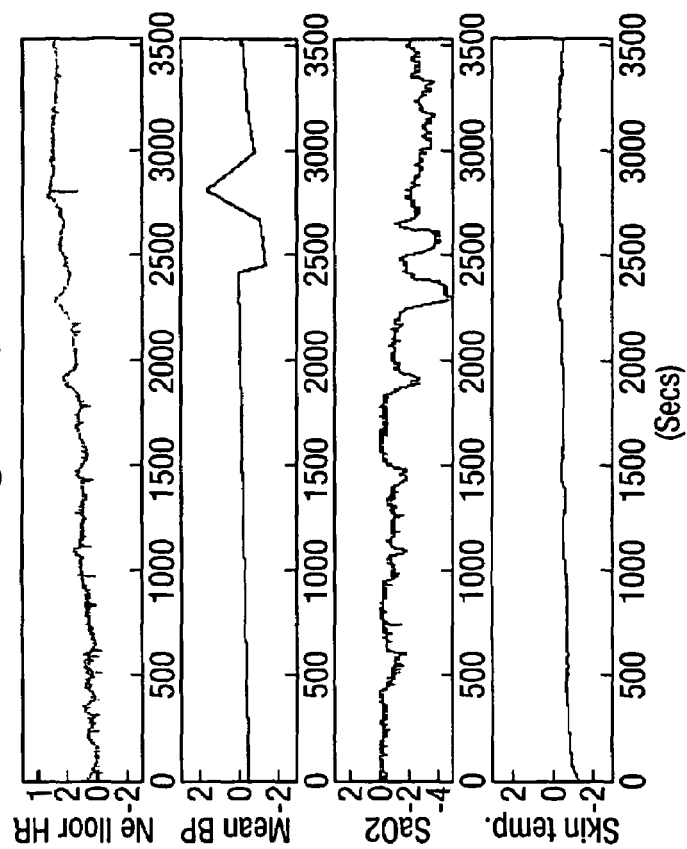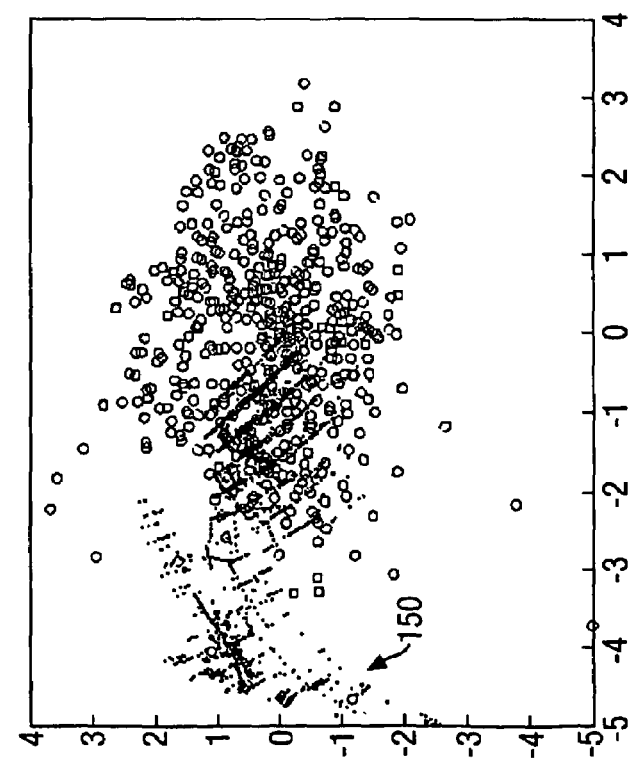
Fig. 15 (A).
Fig. 15 (B).

PATIENT CONDITION DISPLAY

This application is the US national phase of international application PCT/GB02/02550, filed in English on 29 May 2002, which designated the US. PCT/GB02/02550 claims priority to GB Application No. 0113212.5 31 May 2001. The entire contents of these applications are incorporated herein by reference.

This invention relates to the display of a graphical representation of a patient's condition, and in particular to displaying the results of measurements from a variety of sources in a way which allows the patient's overall condition to be recognised easily.

BACKGROUND AND SUMMARY

The condition of patients, particularly, in high dependency care or intensive care, is monitored in a variety of ways. For instance, vital signs such as one or more channels of electrocardiogram (ECG), respiration (for instance measured by electrical impedance pneumography), oxygen saturation (for instance measured by pulse oximetry with a finger probe), blood pressure and skin temperature may all be monitored. These may be regarded as "primary" signals, or parameters, which are measured directly. However, in addition, it is possible to derive from them some "secondary" parameters such as heart rate, heart rate variability, respiration rate and S-T segment elevation/depression (which is measured from the electrocardiogram). Typically the various parameters are collected at different rates, for instance the ECG at 256 Hz, the pulse oximeter signal at 81.3 Hz, the respiration at 64 Hz, the temperature at 1 Hz and blood pressure once every 10 or 20 minutes if measured non-invasively using a blood-pressure cuff. Further, the secondary parameters may be based on some averaging over a period of time.

It has been proposed, as shown in FIGS. 1 and 2 of the accompanying drawings, to display several of the measurements representing a patient's condition together using an integrated monitor. FIG. 1 illustrates a display showing many of the parameters mentioned above, and FIG. 2 illustrates a display of the heart rate and the heart rate variability. However, even with such a wealth of data available to the clinician (or possibly because of it), it can be difficult to see at a glance whether the patient's condition is normal, changing for the better, or, more seriously, for the worse.

In addition the clinical significance of changes of different degree in the different parameters may differ. For instance, a small percentage change in temperature may be much more significant than a small percentage change in blood pressure, or a change in respiration rate may be more significant than a similar change in heart rate. This relative significance may vary depending on the patient's medical problem. Further, the fact that a change in condition may be reflected in one or more parameters and in different ways for different patients and different medical conditions, means that it is very difficult to provide a satisfactory solution by, for instance, simply setting thresholds on each of the displayed parameters. A significant change in condition may be reflected by combinations of parameters, for instance decrease in heart rate combined with a decrease in blood pressure may be serious even though the values per se are not abnormal. It should be noted, though, that the early detection of deterioration in a patient's condition can significantly improve the clinical outcome, and reduce the need for later intensive care, which is thus beneficial both for the patient and for the clinician.

The present invention provides for the display of parameters representing a patient's condition in a simplified way, and which allows the changes in a patient's condition to be seen easily. For instance, the departure of a patient's condition from normality, defined either for that patient or for a group of patients, may be displayed, or equally the progress of a patient from an abnormal condition to a normal condition or vice versa.

In more detail the present invention provides apparatus for displaying a graphical representation of a patient's condition as measured by n parameters, where n>3, comprising a processor which maps data points represented by said n parameters from an n-dimensional measurement space into an m-dimensional visualisation space, where m<n, using a dimensionality reduction mapping, and a display which displays the visualisation space and the data points mapped into it, and which is adapted to the display of dynamically changing values of said parameters by means of the mapping being carried out by a trained artificial neural network.

The parameters may be primary signals as mentioned above, or secondary parameters derived from them. For instance, they may be a respiration measurement, an oxygen saturation measurement, a blood pressure measurement, skin temperature, S-T segment elevation/depression, heart rate variability and respiration rate. Other parameters which can be used are any physical marker or physiological signal or indicator, including, but not limited to:

Physical Signals

Height, Weight, Age (Physical, Mental), Sex, History, Drugs/Medications in use, Body mass index, Body fat, Ethnic origin, Strength, Recovery times after exercise, Endurance/stamina, Cardiovascular function, Coordination, Flexibility, I.Q., Colour (Skin pallor, Retinal), Speech, Skin elasticity, Skin texture, Rashes, Swelling, Oedema, Pain, Shock, Nutritional status, State of hydration, Fatigue, Previous history.

Physiological Signals

EEG (Electrical (frontal, central, mastoid etc), MEG), Heart, Electrical—ECG, Sound, Pressure, Heart rate, Heart rate variability, Cardiac ejection fraction, Cardiac Output Respiration (Rate, Volume, Flow, Pressure, Phase, FEV1 (forced expiratory volume in one second), Gas levels), Blood pressure, (Invasive: Arterial, Central venous, Left atrial, Pulmonary capillary wedge, Right atrial, Pulmonary artery, Left ventricular, Right ventricular, Intra-cranial, Non-invasive, Pulmonary sounds, Pulse transit time, Pulse strength, Pulse rate, Pulse rhythm, Arterial blood oxygen saturation, Venous blood oxygen saturation, CO2 levels in blood, Impedance pneumography, Snoring, Temperature (Core, Peripheral, Blood, Lip), EMG, EOG, Movement (Gait, D.T's, Limb), Sight, Hearing, Smell, Taste, Touch, Throat microphone, Bowel sounds, Doppler ultrasound, Nerves.

Biochemical Signals

Glucose, Insulin, Lactate, Gas levels (Blood, Lungs), Hormones, Alcohol, Thyroid, Blood, Urine, Saliva, Sputum, Stools, Enzymes, Sweat, Interstitial fluid, Cells, Tissue, Hair follicles, 'Recreational' drugs, Proteins, Cholesterol, HIV.

Imaging Signals

Images of, for example:

Brain, Heart/cardiovascular system, Central nervous system, Internal organs Peripheral limbs, Bones.

The dimensionality reduction mapping may be, for instance, a distance preserving mapping or Principal Components Analysis (PCA). Other dimensionality reduction mappings are known. By "distance-preserving mapping" is meant a mapping which preserves some aspect of the geometrical relationship between the data points in the measurement space and in the visualisation space. Thus some aspect of the topology of the measurement space is preserved in the visualisation space. For instance, the mapping can minimise the difference in inter-point distance between pairs of points in the measurement space and the corresponding pairs of points in the visualisation space. An example of such a mapping, which matches the inter-point distances as closely as possible, is a development of Sammon's mapping as described in "Shadow Targets: A Novel Algorithm For Topographic Projections By Radial Basis Functions" by Tipping and Lowe (Artificial Neural Networks, Cambridge 7 to 9 Jul. 1997, IEE conference publication number 440). The distance measure may be any suitable measure, such as the Euclidian distance measure.

Preferably the parameters are normalised prior to mapping, so that the displayed visualisation space spans the desired extent of the measurement space, e.g. to take account of the fact that the different parameters are expressed in different units (for example, temperature in fractions of degrees and blood pressure in terms of mm Hg). The parameters may be normalised using a zero mean, unit variance transformation calculated over the data from the patient (where it is available) or example data from a patient group or another patient, or alternatively the parameters may be normalised using an empirical transformation based on the clinician's knowledge of the significance of changes of different magnitude in the various parameters.

One advantage of using a zero-mean, unit variance transformation is that if a signal drops-out or has to be omitted, e.g. because of excessive noise, it can be replaced by a zero value.

The visualisation space is preferably two-dimensional (i.e. m=2), in which case the display is a straightforward two-axis graphical display on arbitrary axes.

However, a three-dimensional visualisation space, or its representation on a screen is also possible.

The artificial neural network may be trained with data comprising a plurality of sets of parameters from the particular patient being monitored, or by data from a group of patients. Preferably the group is a group of patients with a similar condition to the patient being monitored because "normality" and "abnormality" for a typical patient with heart disease is radically different from "normality" for a patient with a different medical condition, or indeed a healthy person. Obviously when a patient is first-monitored there is insufficient data to train the neural network with data from that particular patient, thus there may be no alternative but to use a neural network trained on a group of patients. Subsequently, after enough data has been collected for that patient, a neural network may be trained with that data, to provide a more personalised mapping.

The data for training the artificial neural network may be selected by pre-clustering the data points in the measurement space. In other words, in a typical situation there may be too many data points for allowing training within a reasonable time period, and instead clusters of data points can be identified and the centres of the clusters used as nominal data points (prototypes) for training the network. Typically, there may be thousands or tens of thousands of data points for continuous monitoring over 24 hours or more for a patient or group of patients. The number of centres or prototypes will typically be greater than 100 but less than 1,000. After the network has been trained, the complete set of data points may be passed through the network to display change in patient condition over the course of collection of all of the data. One way of clustering the data and finding the centres or prototypes is, for instance, the k-means method.

The invention may be applied to human or animal patients, and may be applied to patients having a variety of conditions including disease or injury (actual or suspected), pre and post-operative care, monitoring during traumatic procedures monitoring of the elderly and/or infirm, neonatal monitoring or indeed monitoring in any medical or veterinary environment. The invention may be applied to monitoring in a medical or veterinary establishment or in the home. Thus it may be used as a health monitor in which readings may regularly be taken, and sent automatically to a central collection point for review. The readings may be sent only if they are outside a predefined region of "normality".

The output of the neural network may be used to control automatically the management of the patient, e.g. the administration of drugs, to keep the patient's condition within the predefined region, e.g. the normal region. In a further enhancement, aspects of the management of the patient, e.g. the rate or amount of a drug being administered, or aspects of the environment, may be included as input parameters.

The invention may be embodied by a computer program running on a suitably programmed computer system, or by dedicated systems. Thus the invention extends to a computer program comprising program code means for executing some or all of the functionality of the invention, to a computer storage medium storing such a computer program, and to a programmed computer system embodying the invention.

BRIEF DESCRIPTION OF THE DRAWINGS

The invention will be further described by way of example, with reference to the accompanying drawings, in which.

DETAILED DESCRIPTION OF EXAMPLE EMBODIMENTS

Figure 1:
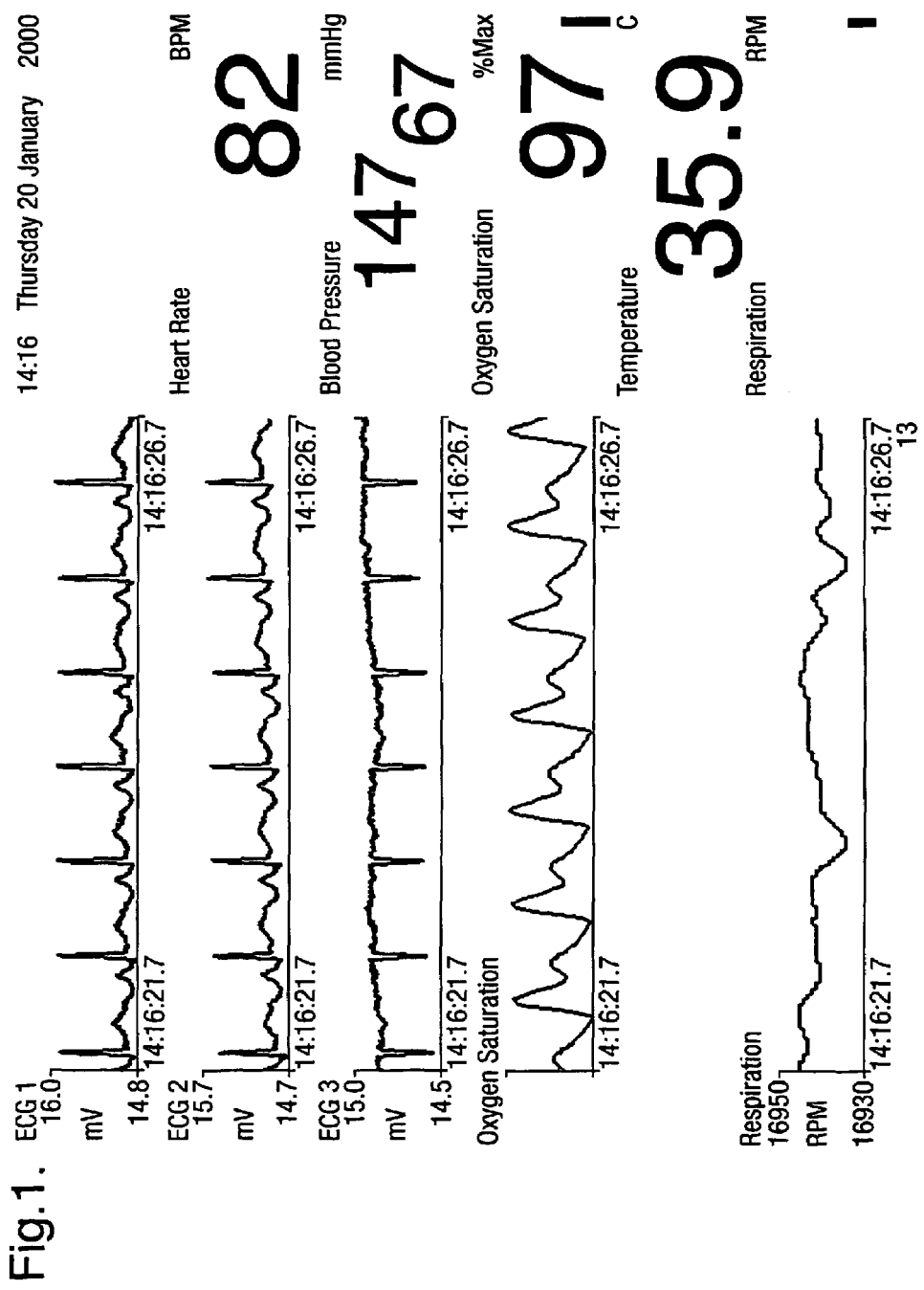
FIG. 1 illustrates a display showing a patient's vital signs.
Figure 2:
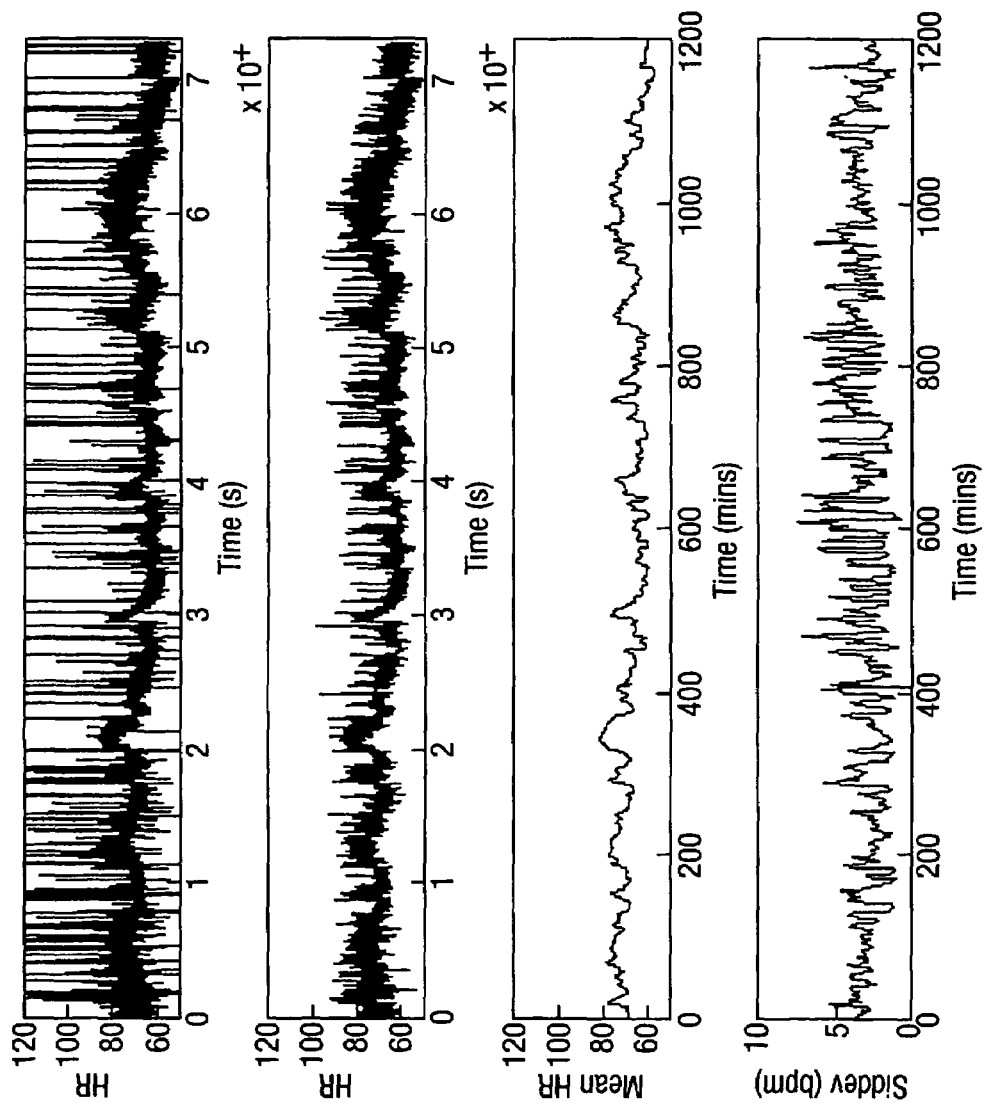
FIG. 2 illustrates a display of heart rate and heart rate variability for a patient.

FIG. 1 illustrates the graphical display from an integrated patient condition monitor. As can then be seen, three channels of ECG, ECG 1, 2 and 3, are shown, together with the oxygen saturation waveform and the respiration waveform. In addition, the values for the non-invasive blood pressure, oxygen saturation waveform and temperature are also shown, together with a measurement of the heart rate, which may be derived from the ECG, the oxygen saturation waveform, or a combination of them. These measurements may be supplemented by other measurements relevant to particular groups of patients. It is known, for instance, that for some group of patients the heart rate variability is an important measurement of patient condition. FIG. 2 illustrates two traces for the heart rate: (i) the raw heart rate, including the sharp spikes associated with the occurrence of ectopic beats, (ii) the filtered heart rate (after the ectopic beats have been removed), a five minute mean heart rate, and the standard deviation of the mean heart rate. Other heart rate variability indices are also known. In addition, although not shown in FIGS. 1 and 2, there are other secondary parameters which may be derived from the primary parameters or signals to give an indication of patient condition. For instance, the S-T segment elevation or depression (measured from the ECG) is significant in patients with heart disease.

Figure 3:
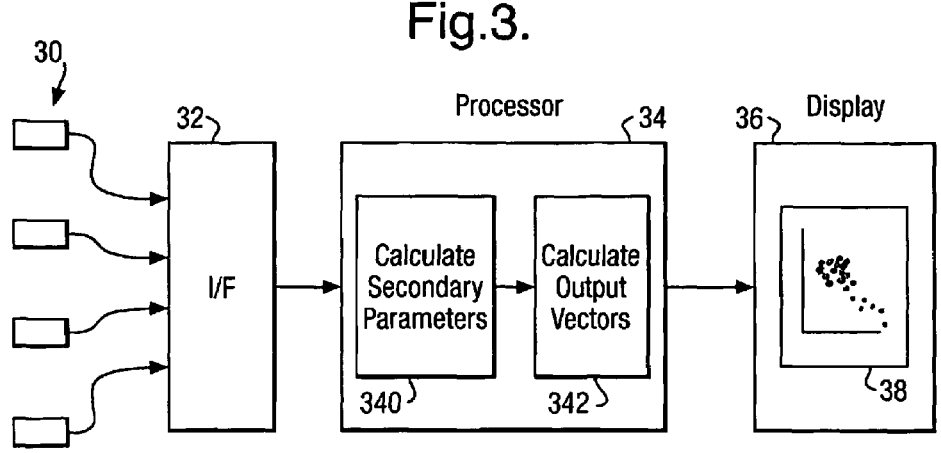
FIG. 3 illustrates schematically an embodiment of the present invention.
Figure 3A:
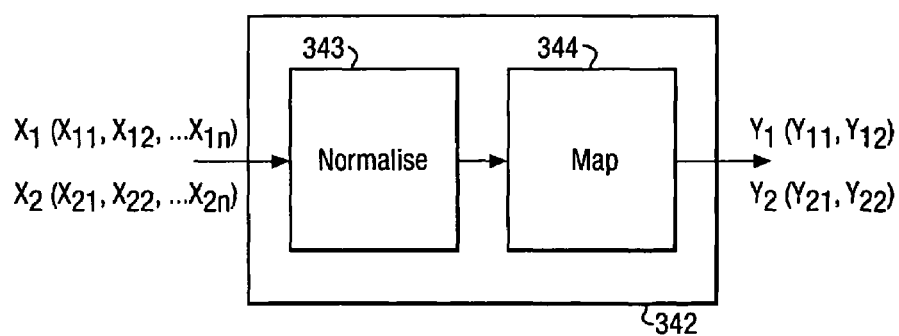
FIG. 3a illustrates in more detail the mapping device of FIG. 3.

FIG. 3 illustrates schematically how, in accordance with the present invention, the primary signals or parameters from the sources (e.g. sensors) and the secondary parameters calculated from them, (which by regarding each parameter as a dimension, can be regarded as defining points in a multi-dimensional measurement space) are mapped into a visualisation space of reduced dimensionality (compared to the measurement space) and displayed. As illustrated in FIG. 3 a plurality of signals e.g. from a plurality of sensors 30, are input via an input interface 32 to a processor 34. The processor 34 includes an analysis device 340 for calculating the secondary parameters from the input signals and a mapping device 342 for reducing the dimensionality of the data into a form in which it can be displayed on display 36. As illustrated in FIG. 3, a two-dimensional display 38 may be used, which means that the dimensionality of the parameters must be reduced to a two-dimensional visualisation space. FIG. 3*a* illustrates this in more detail. The input parameters, which include the primary measurements and the secondary parameters, may be regarded as input vectors $x_1, x_2 \ldots, x_j$ in which each component of the vector is one of the parameters.

FIG. 3*a* illustrates n components for each input vector. The mapping device 342 converts each of these input vectors into an output vector $y_1, y_2 \ldots, y_j$ which has fewer components, for instance two components as illustrated. Thus the output vectors y can be displayed easily on a normal graphical display, such as against the vertical and horizontal axes of a graph. The mapping device 342 is designed to preserve in the output vectors some aspect of the relationship of the input vectors. Thus a significant change in the values of the input vectors will result in a discernable change in the value of the output vectors y. This actually involves two stages as illustrated in FIG. 3*a*, first the normalisation 343 and then the mapping itself (which reduces the dimensionality of the data) at 344. The normalisation is necessary so that the visualisation space correctly covers the range of variation in the input parameters which it is desired to monitor. The normalisation can be statistically based, for instance by looking at an example data set and choosing a normalisation, such as the zero-mean unit-variance normalisation transform, or can be based on a clinician's knowledge, such as knowing that for a particular patient or group of patients a 2.0 degree change in skin temperature is equivalent in significance to a 50 mm Hg change in blood pressure.

The normalisation is also effective to place data points deriving from a patient in a normal state in some predefined region of the displayed visualisation space, e.g. the centre, and data points derived from a patient in an abnormal condition somewhere else—e.g. at the edge.

Figure 6:
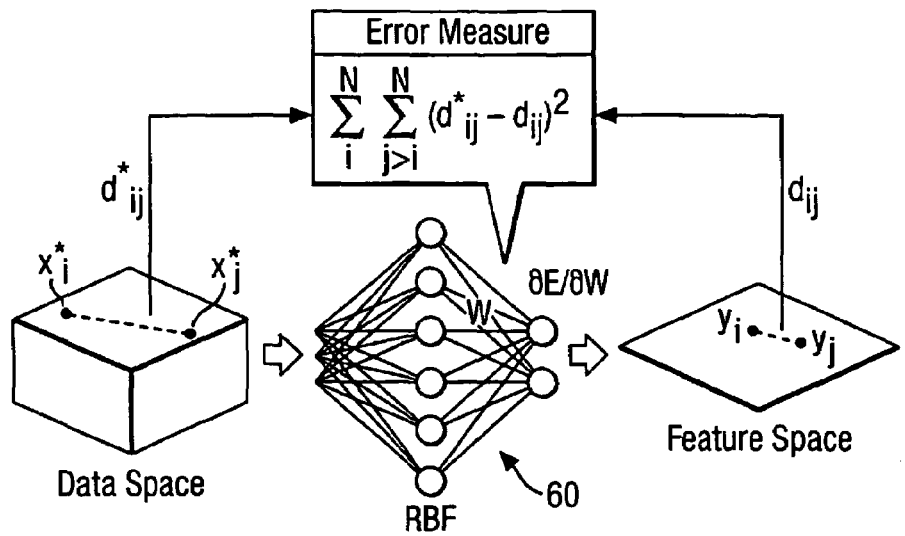
FIG. 6 illustrates schematically the training of an artificial neural network.

The normalised parameters are then mapped to the output vectors in a way which is designed to preserve or match as closely as possible some aspect of the topography of the input vectors. In this embodiment Sammon's mapping is used so that the inter-point (Euclidian) distances between the points represented in the measurement space by the input vectors are as close as possible to the corresponding inter-point distances in the output vectors. As illustrated in FIG. 6 this is achieved by minimising an error measurement which is the sum of the squares of the differences between the inter-point distances. With the present invention this is achieved by using an artificial neural network 60 represented schematically in FIG. 6 which is trained on a set of data points which can be derived from a single patient, such as the patient being monitored, or from a group of patients. In this embodiment, as illustrated in FIG. 6, a Radial Basis Function neural network is used.

Figure 4:
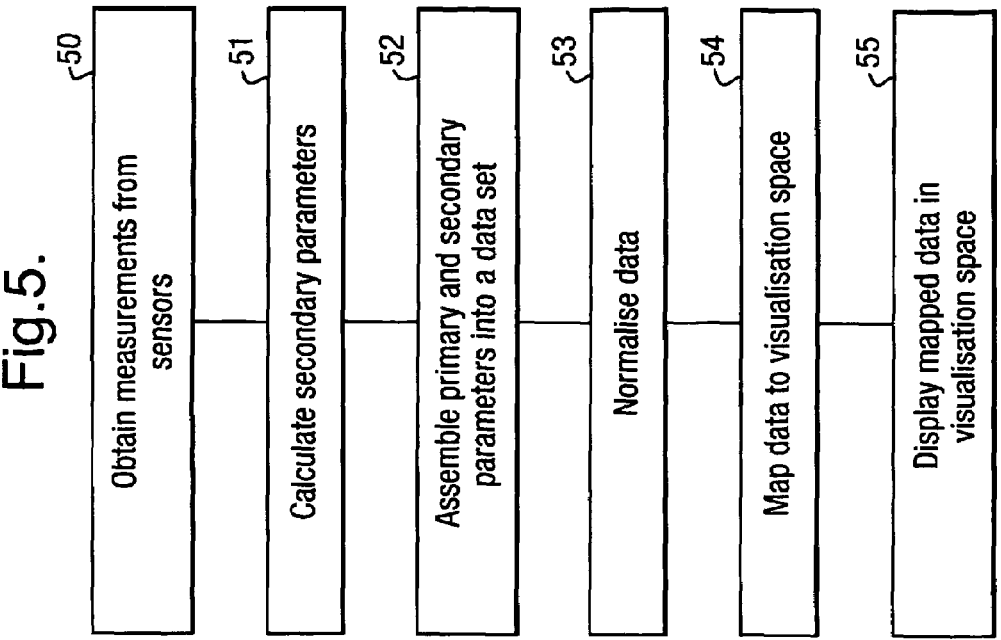
FIG. 4 illustrates schematically the process of training an artificial neural network and mapping points in accordance with an embodiment of the present invention.
Figure 7A:
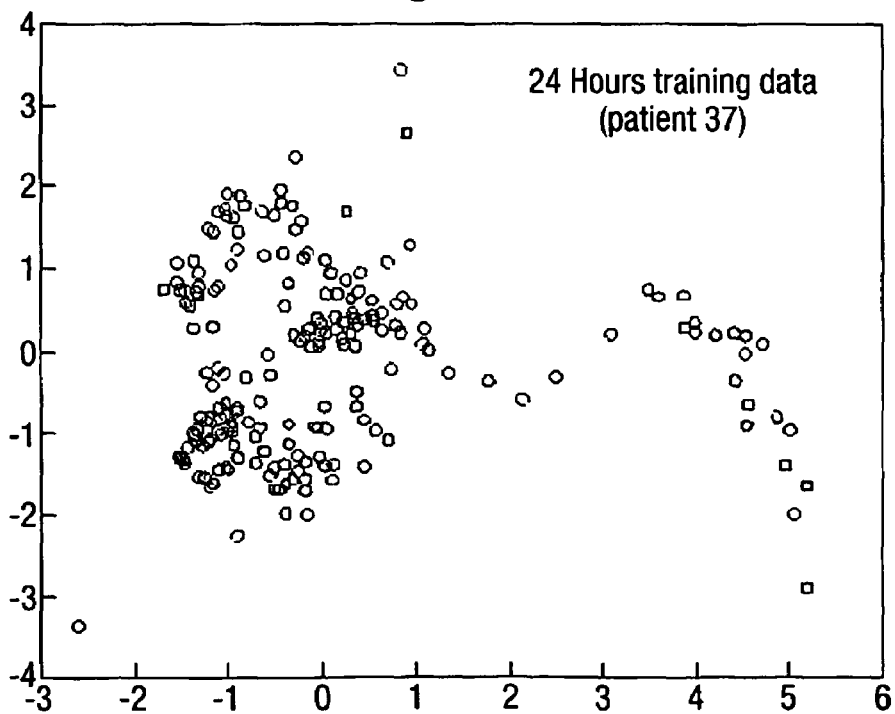
FIGS. 7a to 7g illustrate the display of data from a particular patient using an embodiment of the present invention.
Figure 7B:
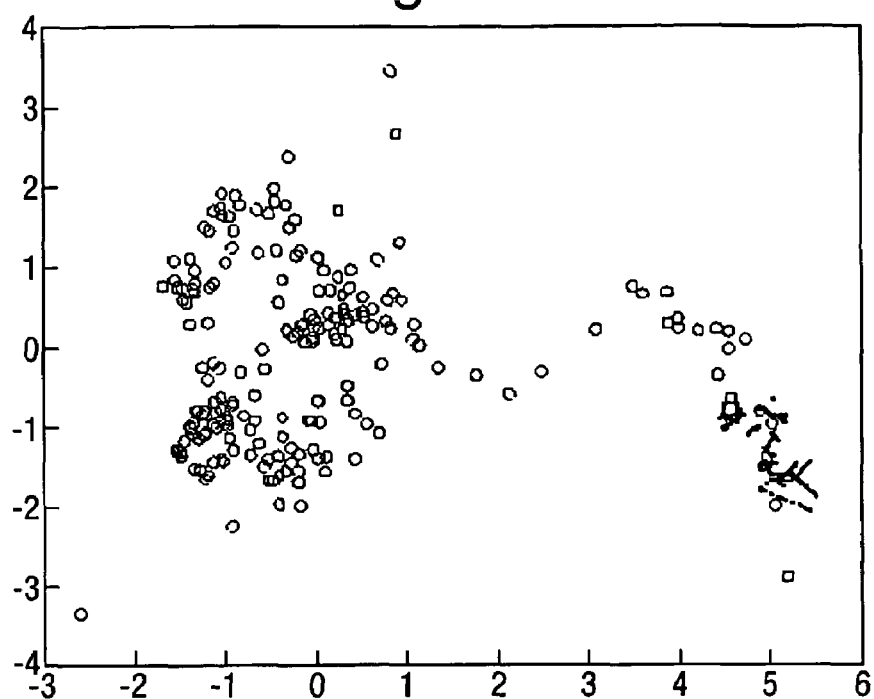
Figure 7C:
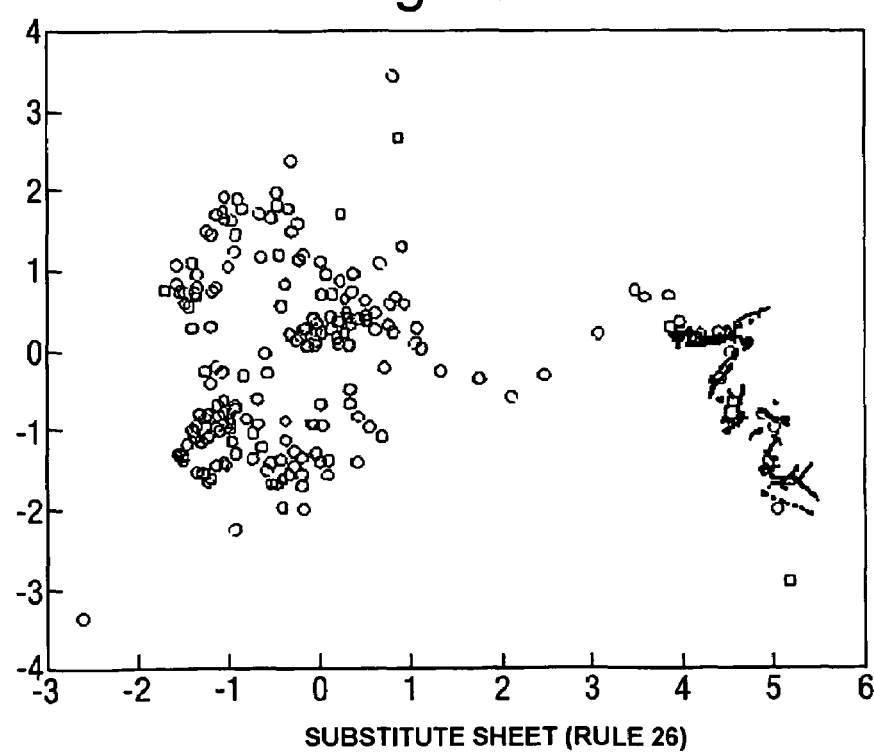
Figure 7D:
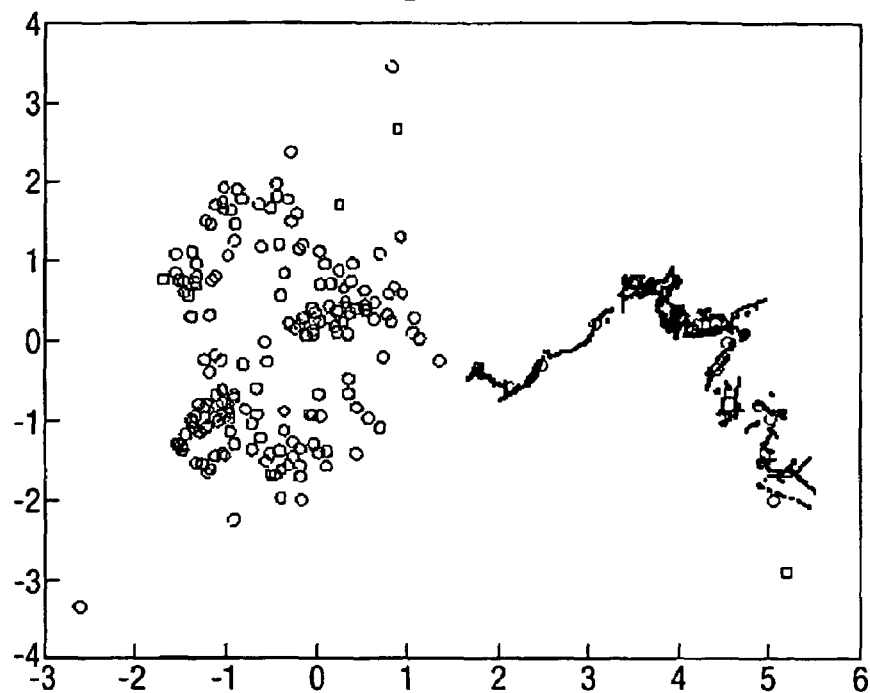
Figure 7E:
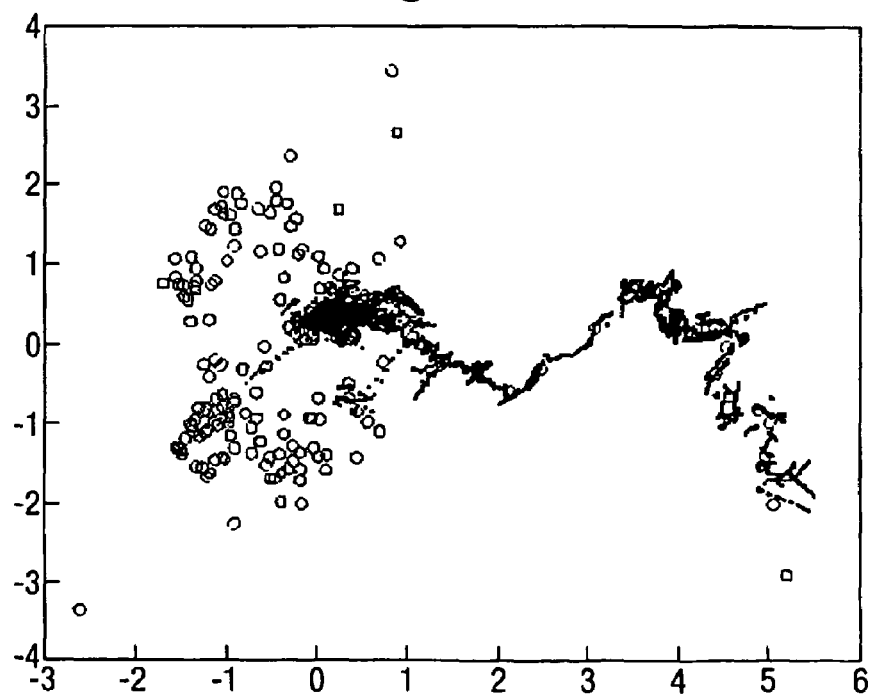
Figure 7F:
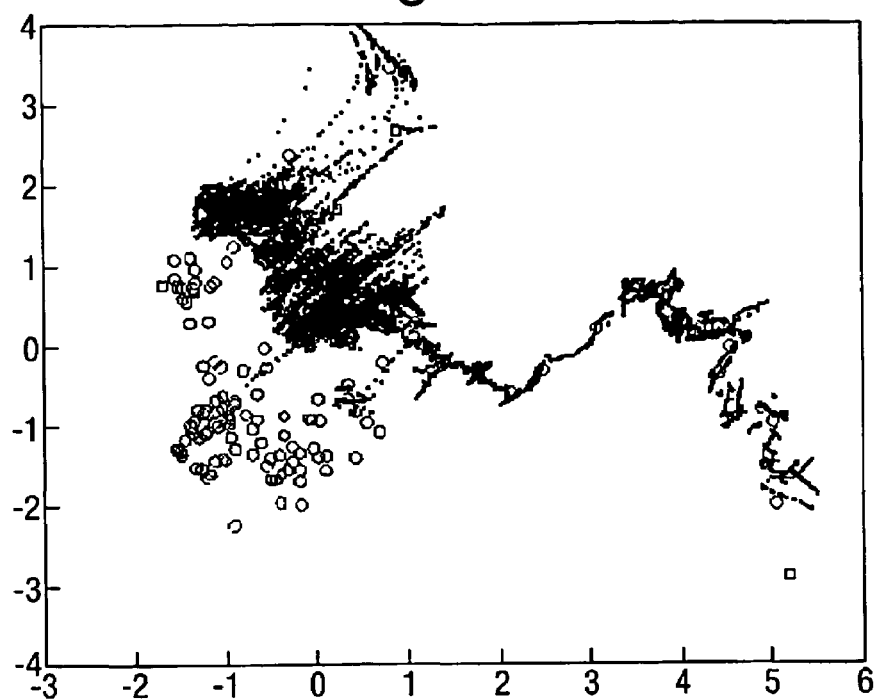

The training process is illustrated schematically in FIG. 4. Measurements representing primary parameters, are obtained at step 40 from a plurality of sources. Secondary parameters, if necessary, are then calculated from the primary parameters at step 41. These are assembled into a data set at step 42 and then these are normalised to give the input vectors x* at step 43. Typically this process would result in an enormous amount of data and it would take a long time to use this data to train an artificial neural network. The amount of data is therefore reduced, in this embodiment by pre-clustering the data at step 44. The data may be pre-clustered using the k-means method which is a well known iterative way of examining a set of data points repeatedly and deriving from them a set of prototypes or cluster centres. In this case the initial choice of cluster centres was a set of patterns randomly picked from the training data set. In the iterative process clusters are moved so that they are optimally placed with respect to the data points. The centre points of the clusters are then regarded as nominal data points which can be used to train the artificial neural network as illustrated at step 45. In this case the initial weights for the neural network were small random values between −0.01 and +0.01. FIG. 7*a* illustrate a display of 24 hours of training data taken from an example patient. Thus the points shown in FIG. 7a are the points in the visualisation space which correspond to the cluster centres or prototypes in the measurement space.

Figure 5:
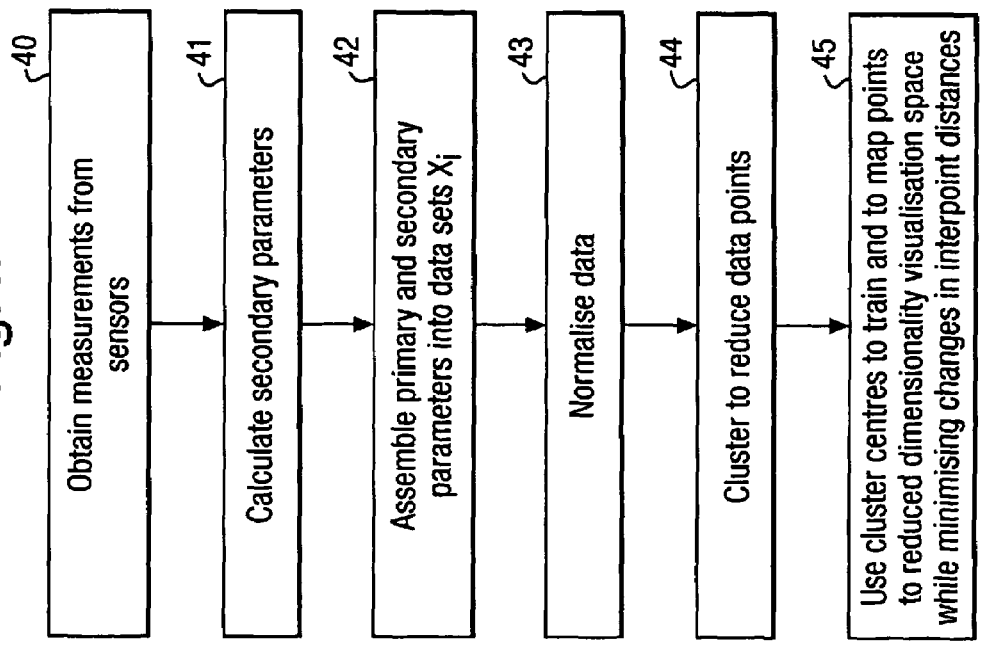
FIG. 5 illustrates schematically the monitoring process according to an embodiment of the present invention.

Once the neural network has been trained to produce the mapping from n dimensions to 2-D, the complete data, rather than just the cluster centres or prototypes, can be mapped to the visualisation space using the neural network and, of course, new measurements coming from the patient on a continuous basis can also be normalised and mapped to show the patient's current condition. Thus, as illustrated in FIG. 5, the primary and secondary parameters are obtained in steps 50 and 51, assembled into data sets at step 52, normalised at step 53 and then mapped using the neural network at step 54 and displayed at step 55.

FIGS. 7b to 7g illustrate the display of the data points themselves overlaid on the display of the visualisation space defined by the cluster centres or prototypes of FIG. 7a. It can be seen at FIG. 7b (the first hour of 24 hours of data) that the data points which are early in the set of data are positioned at one edge of the visualisation space, indicating that the patient's condition was abnormal at that stage. Through the course of FIGS. 7c (first 3 hours), 7d (first 6 hours), 7e (first 9 hours) the patient's condition approaches the area where most of the points derived from the training set are located, representing normality for that patient. Data points continue to be added through FIGS. 7f (first 15 hours) and 7g (all 24 hours) illustrating that the patient's condition stabilises such that the data points are mapped to the region just left of centre in the visualisation space, with occasional departures above and below that space.

It can be seen, therefore, that the progress of a patient's condition can be visualised very easily using this mapped display. Any departure from normality for that patient would result in a succession of data points departing from the "normal" region just to left of centre of the visualisation space. Further, if a patient's condition is changing, such as during administration of a drug or some other medical procedure, one would expect to see a particular trajectory across the visualisation space. Departures from that trajectory would represent an abnormal response to the medical procedure, for instance that the patient's condition is deteriorating. An alarm for alerting staff to departures of the patient condition outside that area or trajectory can also be included.

It will be clear, furthermore, that it is possible to modify the apparatus to include an alarm which responds to data points being plotted outside a pre-defined region of "normality" in the visualisation space or off a predefined normal trajectory (corresponding to an expected change in patient condition). This will be explained in more detail below with respect to a visualisation space defined for a group of patients, although it is equally applicable to the visualisation space shown in FIG. 7 for a particular patient.

In FIG. 7 a set of data points from a patient is used (after pre-clustering) to train the artificial neural network. The trained network may then be used to continue to monitor that patient by inputting new data points to it and having them mapped and displayed in the visualisation space. Clearly, though, when a patient is first monitored, no prior data may be available for that patient. Further, there may be insufficient data for several hours to train the artificial neural network, and in any event the network can only be adequately trained after a sufficient amount of data representing normality for that patient has been obtained. For that initial period, therefore, it is necessary to map the data points to the visualisation space by using an artificial neural network which has already been trained. This can be achieved by training an artificial neural network on data from a representative group of patients for a particular condition. It should be noted that training the artificial neural network using data from healthy people is unlikely to be satisfactory since their data is unlikely to span the necessary range of the measurement space. Further, patients with different conditions may, again not provide data which is sufficient to span the measurement space desired for the patients to be monitored.

Figure 7G:
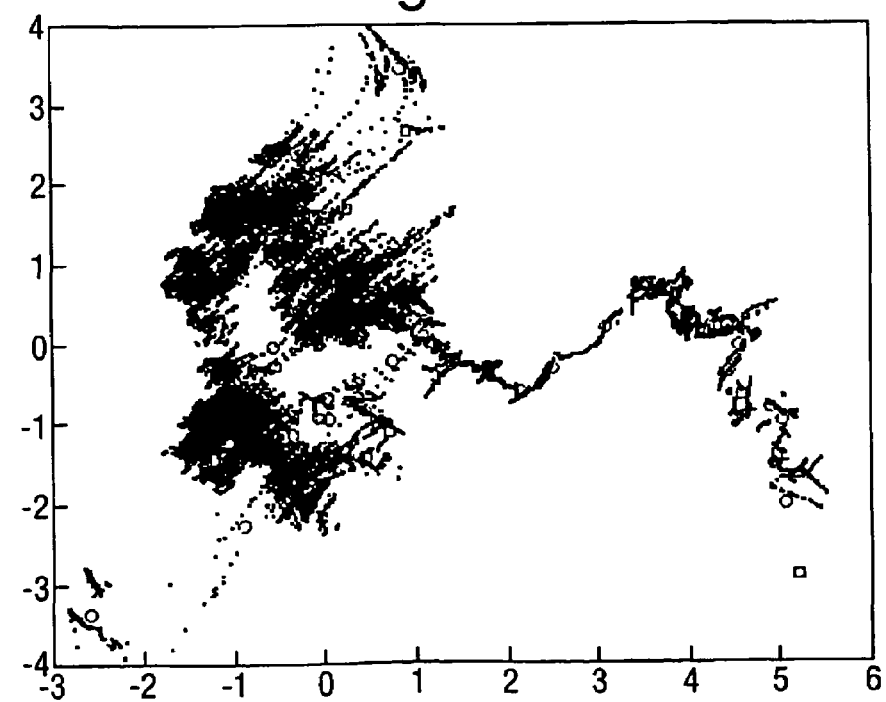
Figure 8:
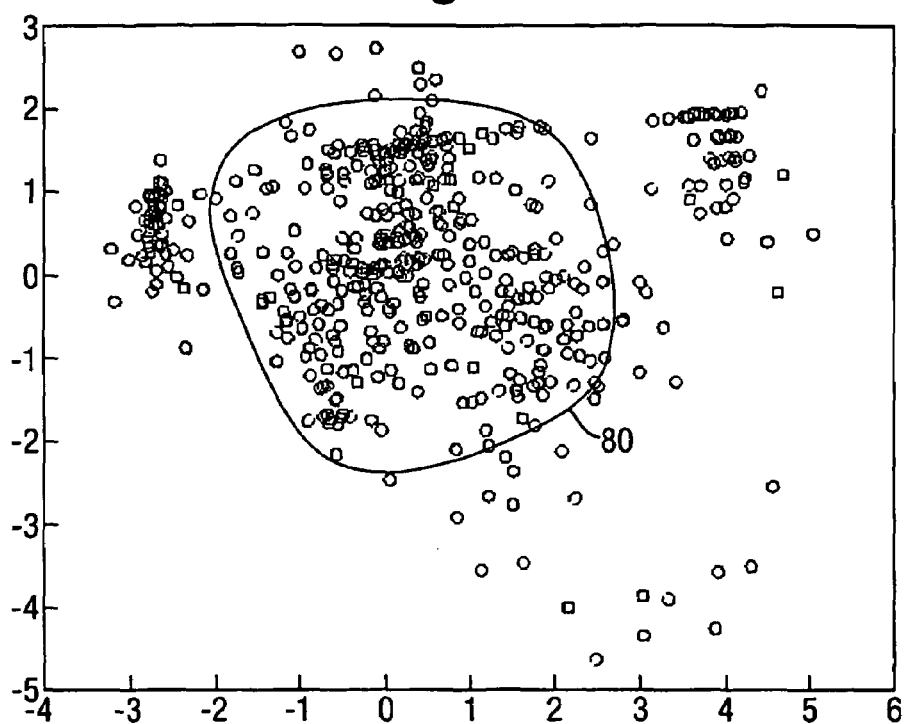
FIG. 8 illustrates the display of visualisation space and training data for a group of patients.
Figure 9:
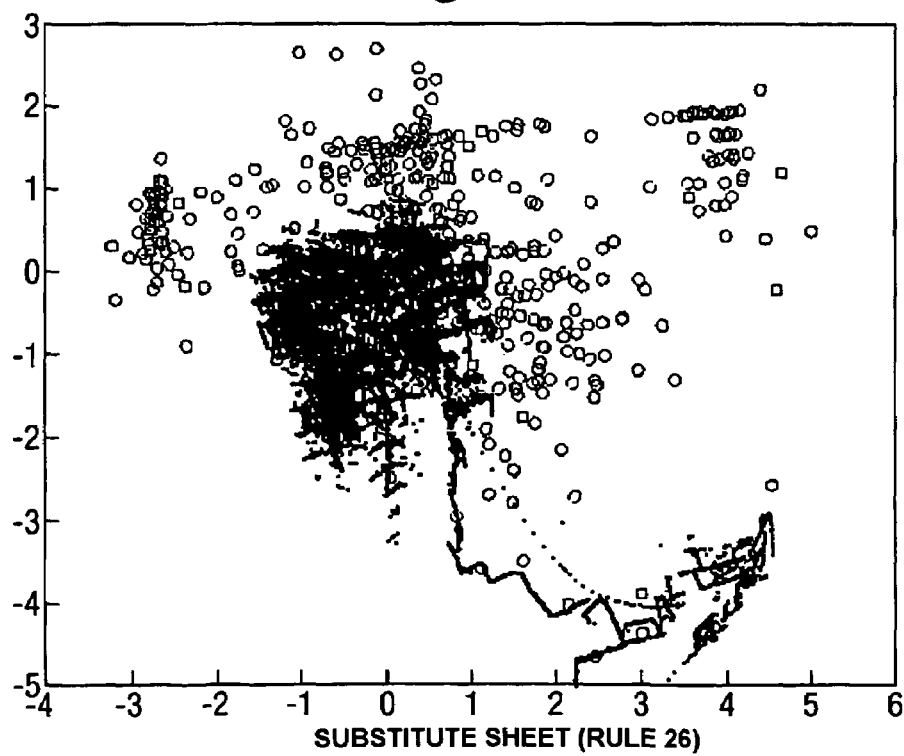
FIG. 9 illustrates the display of a patient's condition in the visualisation space of FIG. 8.

FIG. 8 illustrates a visualisation space showing points which have been mapped using data from several patients in a group (which data is normalised and may be pre-clustered as above if necessary). It can be seen that much of the data is clustered in the central region of the display, and it is therefore possible to define a boundary 80 within which the patient condition is regarded as being normal for that group, and outside of which the patient condition is regarded as being abnormal. The data from a particular patient can be mapped using the artificial neural network trained with the data from the patient group and then displayed on the visualisation space for the group. FIG. 9 illustrates a plot of a particular patient's condition on the visualisation space for the group. FIG. 9 is the data from the same patient as FIG. 7g (patient 37) but whereas in FIGS. 7b to g, the n-dimensional data is mapped onto the visualisation space defined by that patient only (FIG. 7a), in FIG. 9, the same n-dimensional data is mapped onto the visualisation space defined by that patient group (i.e. in this case patient 37 and 5 other patients, including patient 36—FIG. 10, patient 52—FIG. 11—and patient 56—FIG. 12). Similar trajectories/distribution of points are seen in FIGS. 7g and 9, the differences being due to the difference in the construction of the visualisation space (single patient vs group of patients).

Figure 10:
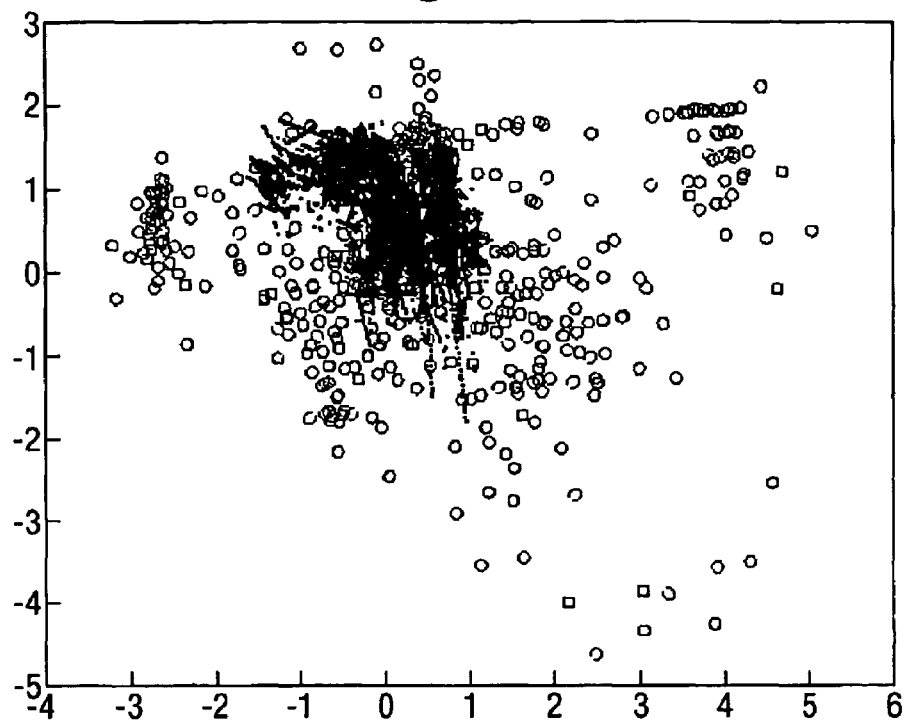
FIG. 10 illustrates the display of another patient's condition in the visualisation space of FIG. 8.
Figure 11:
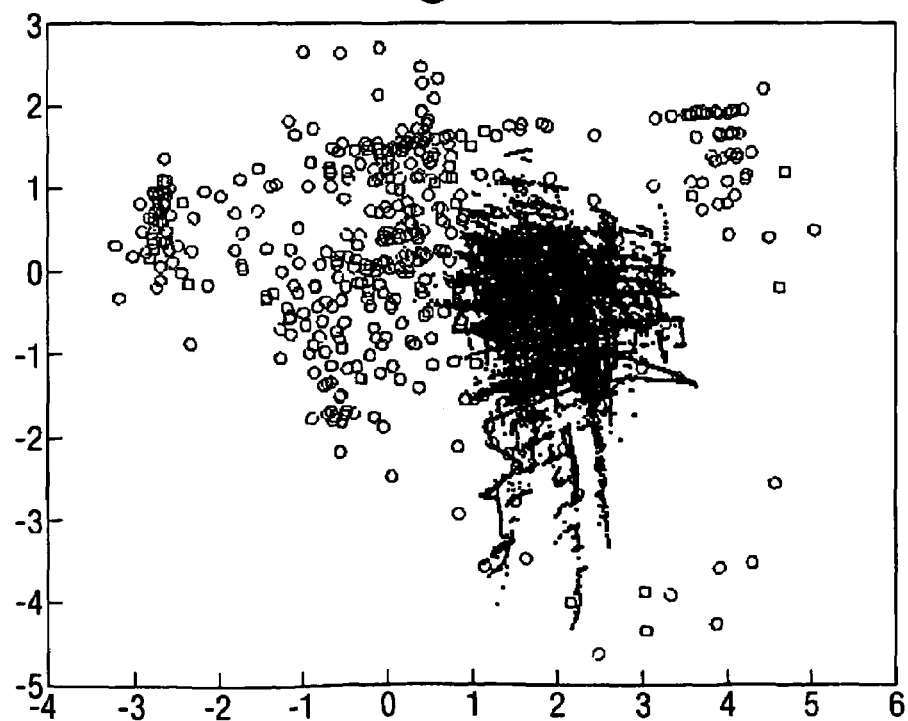
FIGS. 11 and 12 illustrate the display of other patients' conditions in the visualisation space of FIG. 8.
Figure 12:
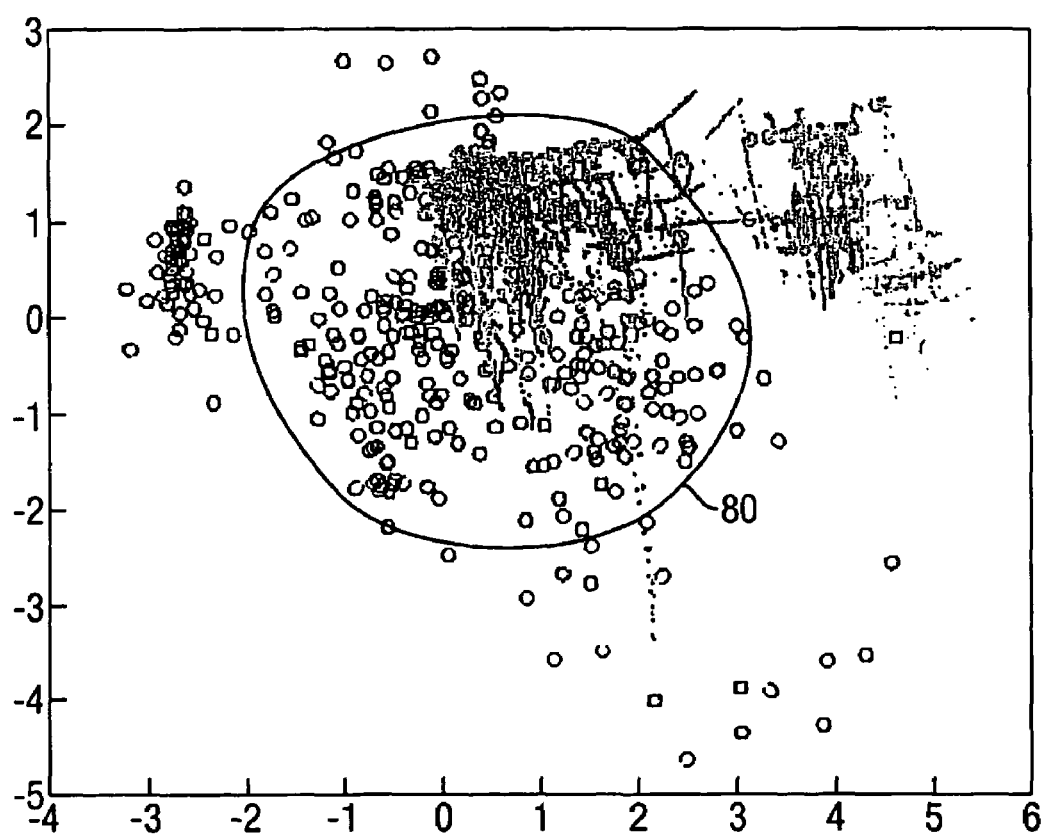

FIG. 9 (or 7a to 7g) represents an improving patient with a heart condition. FIGS. 10 and 11 (patients 36 and 52) are "normal" patients within the group of patients with heart problems. FIG. 12 (patient 56) represents a patient who starts out as "normal" for that group (the region within boundary 80) but deteriorates during the course of monitoring to the right-hand part of the plot. An alarm can be generated once the boundary of normality has been crossed.

The data used in FIG. 7 was normalised readings of four parameters: heart rate, blood pressure, oxygen saturation and skin temperature, taken for an individual patient from a coronary care unit over a period of 24 hours resampled at a sampling rate of once a second. FIGS. 8 to 12 are based on a data set of the same parameters as in FIG. 7 for periods of 24 hours for six patients, all of whom were patients in a coronary care unit. FIGS. 13 to 20 are based on resampled data sets of measurements of the same four parameters for one to twelve hours, for 14 patients having acute dyspnoea, congestive heart failure or post myocardial infarct.

Figure 13:
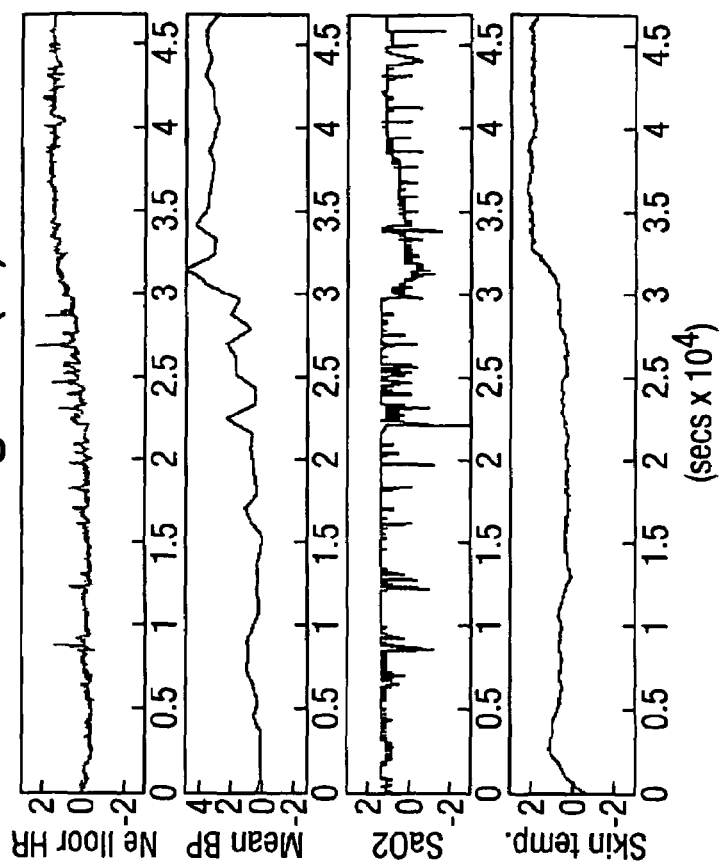
FIGS. 13(A) and (B), 14(A) and (B), 15(A) and (B) and 16(A) and (B) show data for different individual patients plotted on a visualisation space for a group of patients and individual plots of the four parameters under consideration.
Figure 13:
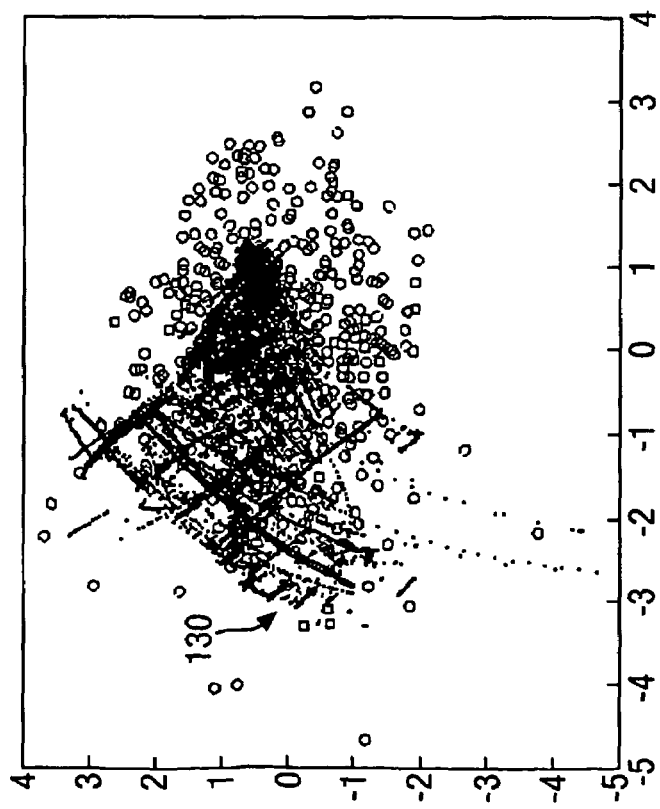
Figure 16:
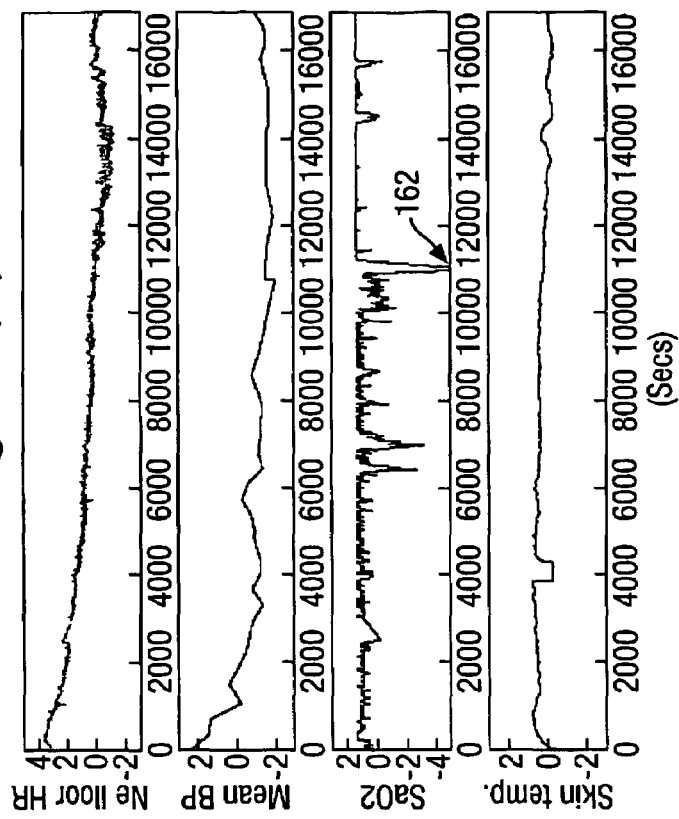
Figure 16:
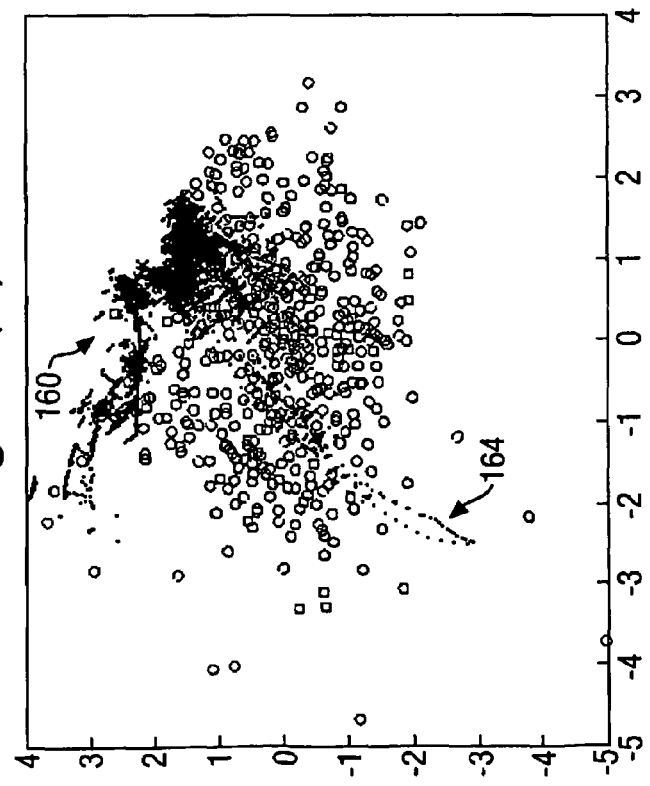

FIGS. 13(A) and (B) illustrate the same data as in FIG. 12 (for patient 56) plotted on a visualisation space in which the mapping was derived using a training data set from a different group of (abnormal) patients. Again "normality" is in the middle of the visualisation space. The patient starts off with "normal" heart rate, blood pressure, skin temperature and oxygen saturation as can be seen from the individual plots of these parameters in FIG. 13(B). However, in the last third of the time plotted, all four parameters change as the patient's condition deteriorates and this can be seen in the visualisation space of FIG. 13(A) as the departure labelled 130 towards the left-centre of the space. In the data sets used for in FIG. 13, and also FIGS. 14 to 20 the heart rate is measured in beats-per-minute, the blood pressure in mm Hg, the temperature in ° C. and the oxygen saturation in percentage points. Since these data have been normalised using the zero-mean, unit-variance transform, a "normal" value in each case is 0.0. On the figures the normalised values are plotted with the vertical axis being labelled in number of standard deviations for the set of data, and the horizontal axis in seconds (every five seconds for FIGS. 14 to 19).

FIGS. 14(A) and (B) illustrate respectively data plotted on the visualisation space and the individual parameter plots for a patient whose condition remains normal over the course of the measurements.

FIGS. 15(A) and (B) illustrate respectively the data plotted on the visualisation space and the individual parameter plots for a patient whose heart rate rises and oxygen saturation dips (down to 75%), this being shown in the visualisation space as the departure labelled 150 to the left of the space. This patient required transfer to an intensive care unit.

FIGS. 16(A) and (B) illustrate corresponding plots for a patient whose condition started as abnormal (high heart rate and blood pressure) and became normal, resulting in trajectory 160 in the visualisation space of FIG. 16(A). However, the patient's oxygen saturation suddenly dipped (at point 162 on the oxygen saturation plot of FIG. 16(B)), when their oxygen mask was removed. This is seen as departure 164 towards the bottom left on the visualisation space of FIG. 16(A).

A further indication of the patient's condition may be obtained by deriving an "index of novelty" of each point, based on the distance in the multi-dimensional measurement space of that point from the predefined "normal" point. After normalisation with a zero-mean transform, the "normal" point will be the origin, i.e. the point with coordinates (0, 0, 0, 0 . . . ) in the measurement space. The index of novelty may be computed using the method of Parzen Windows as disclosed in "Novelty Detection for the Identification of Masses in Mammograms", Tarassenko et. al., Procs. $4^{th}$ IEE Int. Conf. on Artificial Neural Networks, Cambridge, June 1995, pp 442–447, where novelty is assessed by summing the distance between a data point and each of a set of prototype points representing normality (e.g. the 80% of the prototype points which are closest to the origin).

This index of novelty may be used to trigger an alarm condition, for instance if it is greater than a predetermined threshold. The threshold may be defined, for example, as being a boundary encompassing the normal prototypes.

Figure 19A:
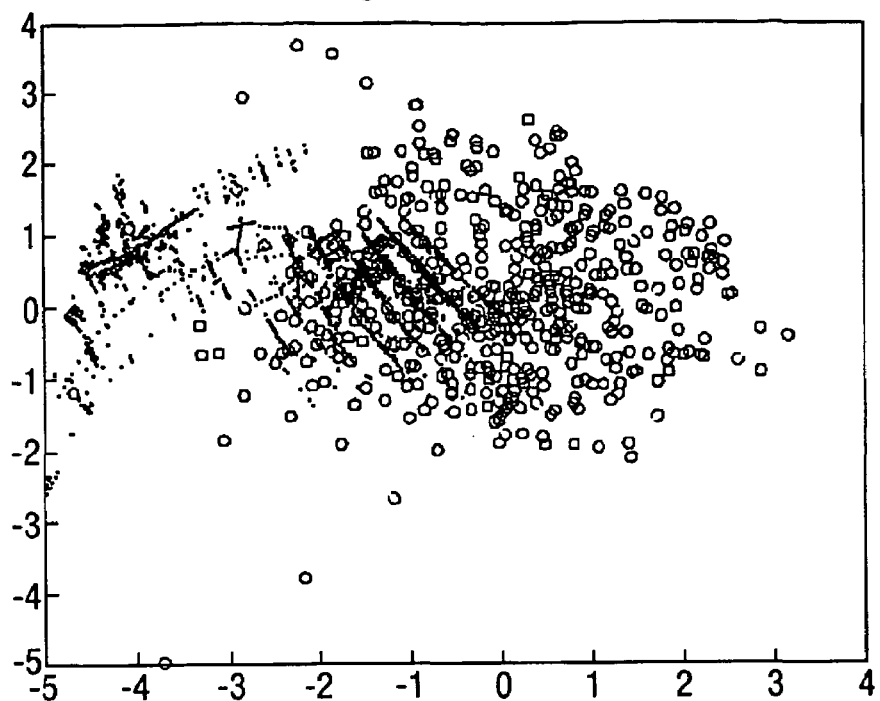
Figure 20A:
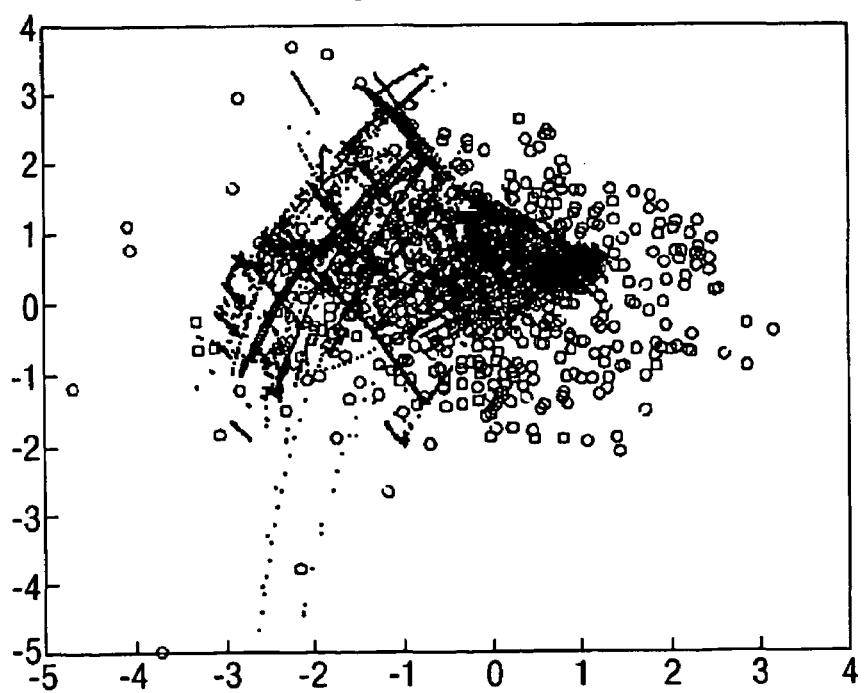
Figure 19B:
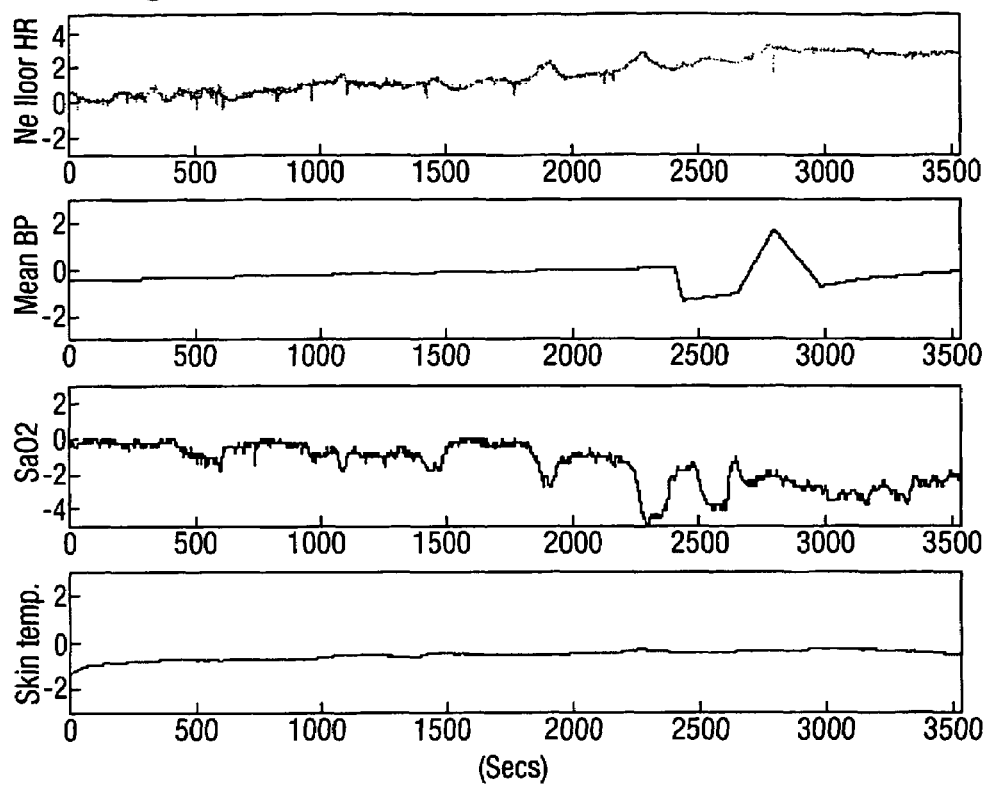
Figure 19C:
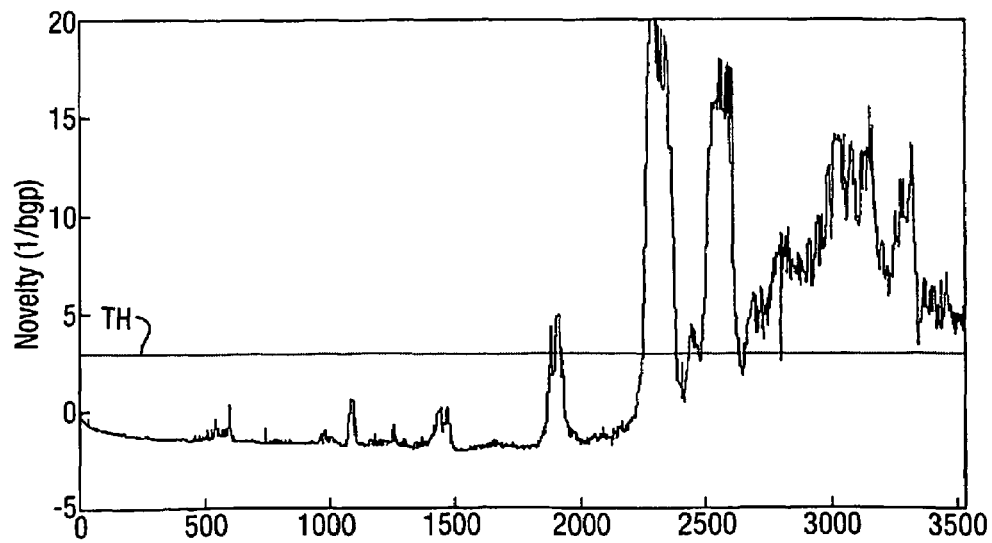
Figure 20B:
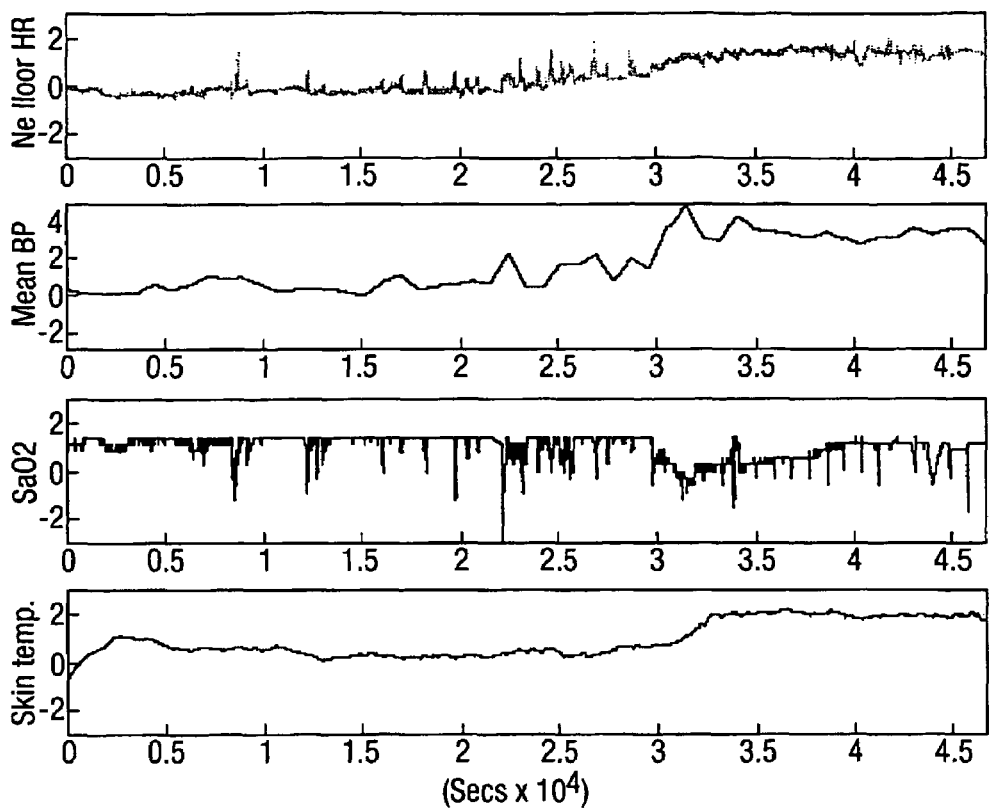
Figure 20C:
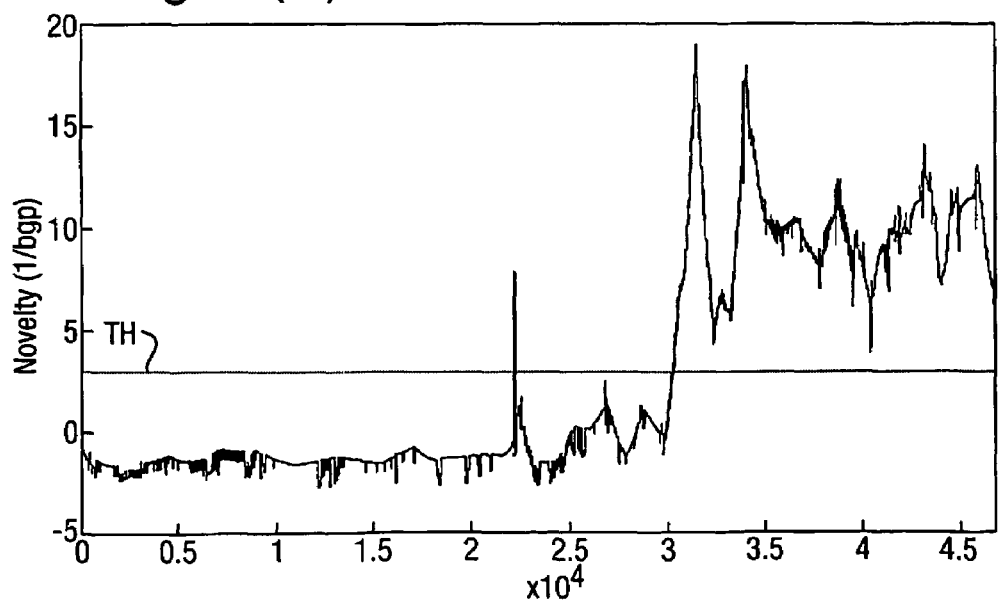
Figure 21:
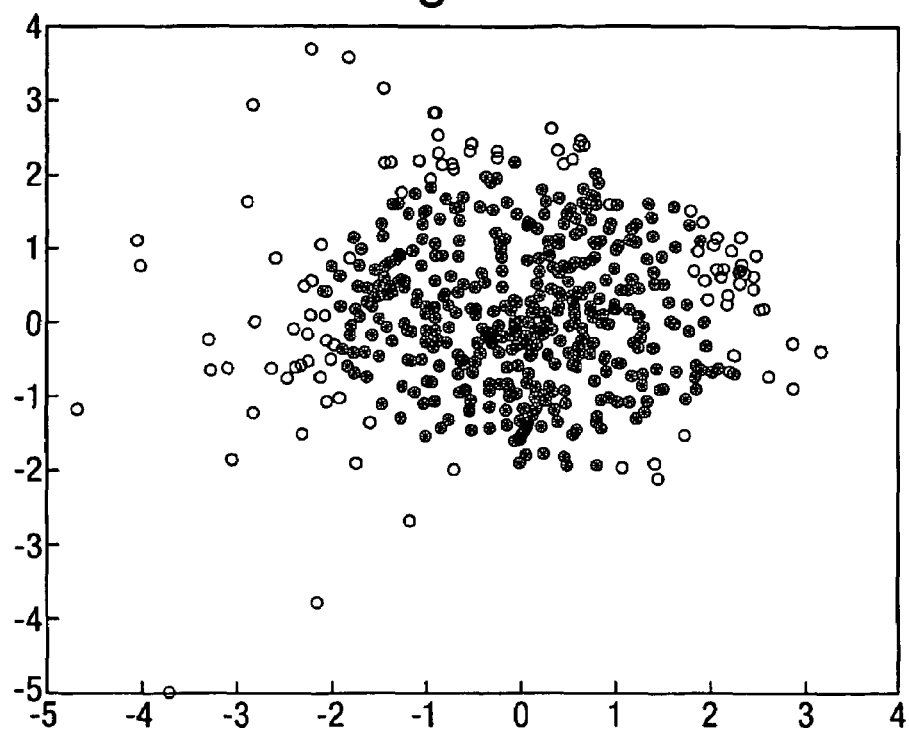
FIGS. 21 and 22 show the training data set for the data used in FIGS. 13 to 20, plotted on the visualisation space and coloured according to the value of the index of novelty.
Figure 22:
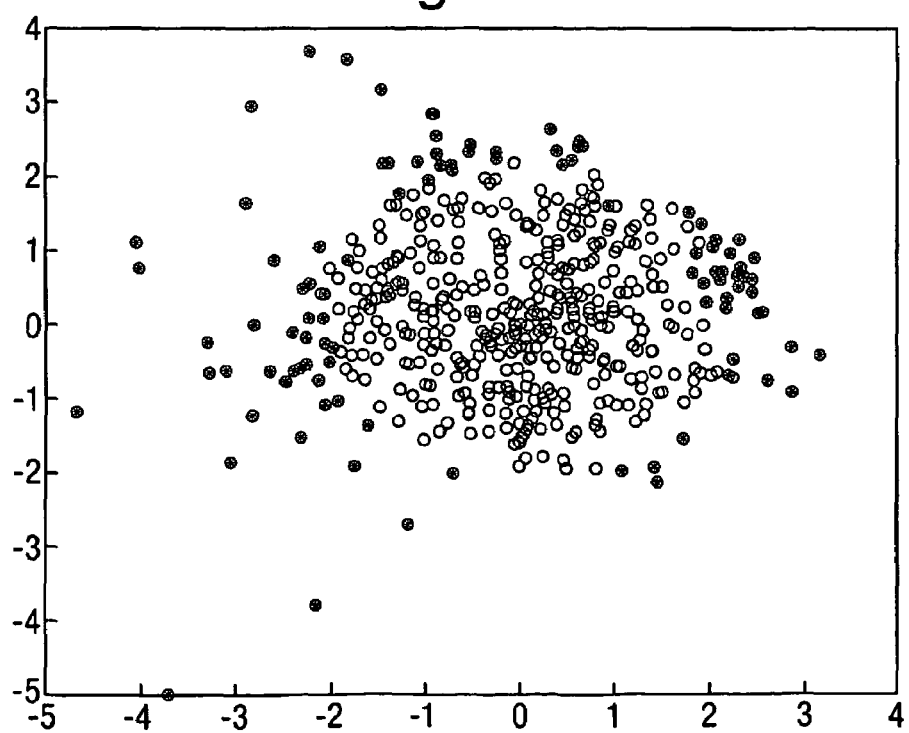

This index of novelty may be displayed on a plot as illustrated in FIGS. 21 and 22 for the prototype points (the training set used for FIGS. 13 to 20). In FIG. 21 the 80% of prototype points closest to (0, 0, 0, 0) in the measurement space are shown in black and in FIG. 22 the remainder are shown in black (though in practice green and red are used respectively).

In FIGS. 17 to 20 the points in the visualisation space (a) are shown, together either with the plots (b) of the four normalised individual parameters (heart rate, blood pressure, skin temperature and oxygen saturation) with time, and the index of novelty plotted against time is presented in the bottom right-hand corner of the display (c).

The alarm condition for the patient is preferably not triggered only by crossing the threshold (shown by line TH in FIGS. 17 to 20), but by a combination of the time and extent to which the threshold is crossed. This avoids triggering by brief artefacts, as are visible, for example, in FIGS. 18 and 20. This may be achieved by integrating the area between the plot and the threshold, and only triggering the alarm when this area exceeds a certain amount.

The index of novelty may be calculated from the unconditional probability density function p(x), where x is the vector of parameters (in this case using their normalised values). This may be estimated using the standard method of Parzen Windows referred to before, where:

$$p(x) = \frac{1}{n(2\pi)^{d/2}\sigma^d} \sum_{m=1}^{n} \exp\left\{-\frac{1}{2}\frac{\|x-x_m\|^2}{\sigma^2}\right\}$$

One spherical Gaussian kernel for each normal prototype $x_m$

σ is a smoothing parameter which is the same for all normal prototypes $x_m$, taken as the average distance between a prototype pint and its ten nearest neighbours d is the dimensionality of the data, 4 in this case as four parameters are measured.

Novelty is then calculated as 1/log p(x). Thus $\|x-x_m\|$ is a measure of the distance between the current data point and the $m^{th}$ normal prototype in the training set of which there are n.

Figure 17A:
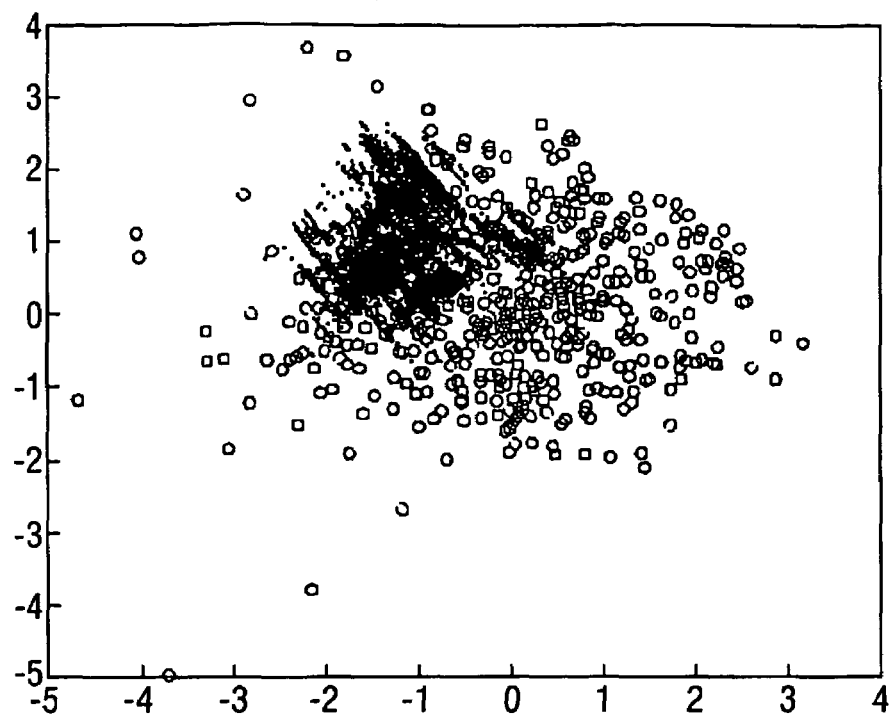
FIGS. 17 to 20 show data plotted for different patients on the visualisation space (a), as individual parameter plots (b) and the index of novelty (c)
Figure 18A:
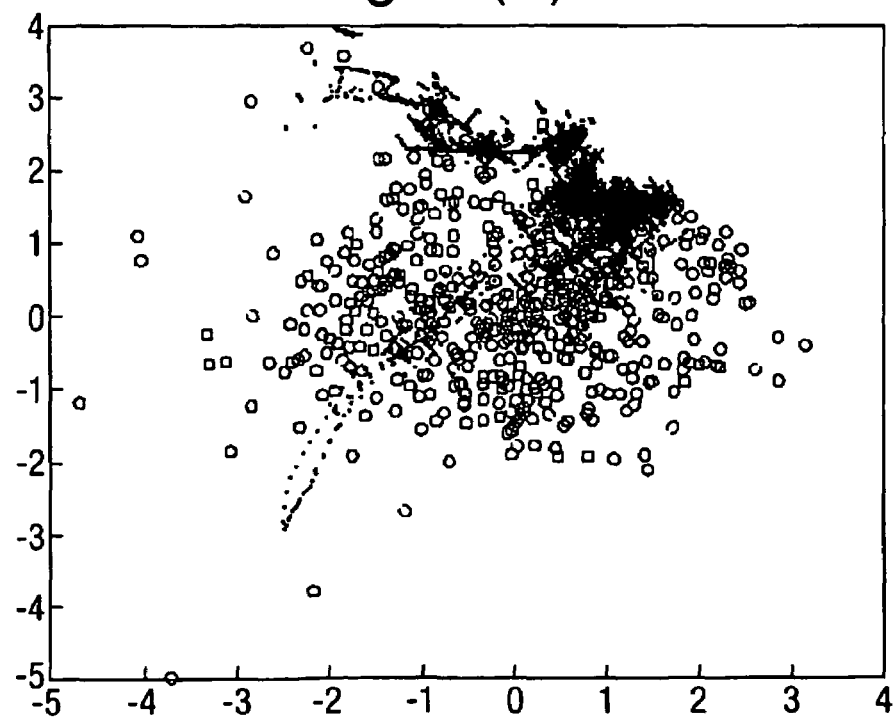
Figure 17B:
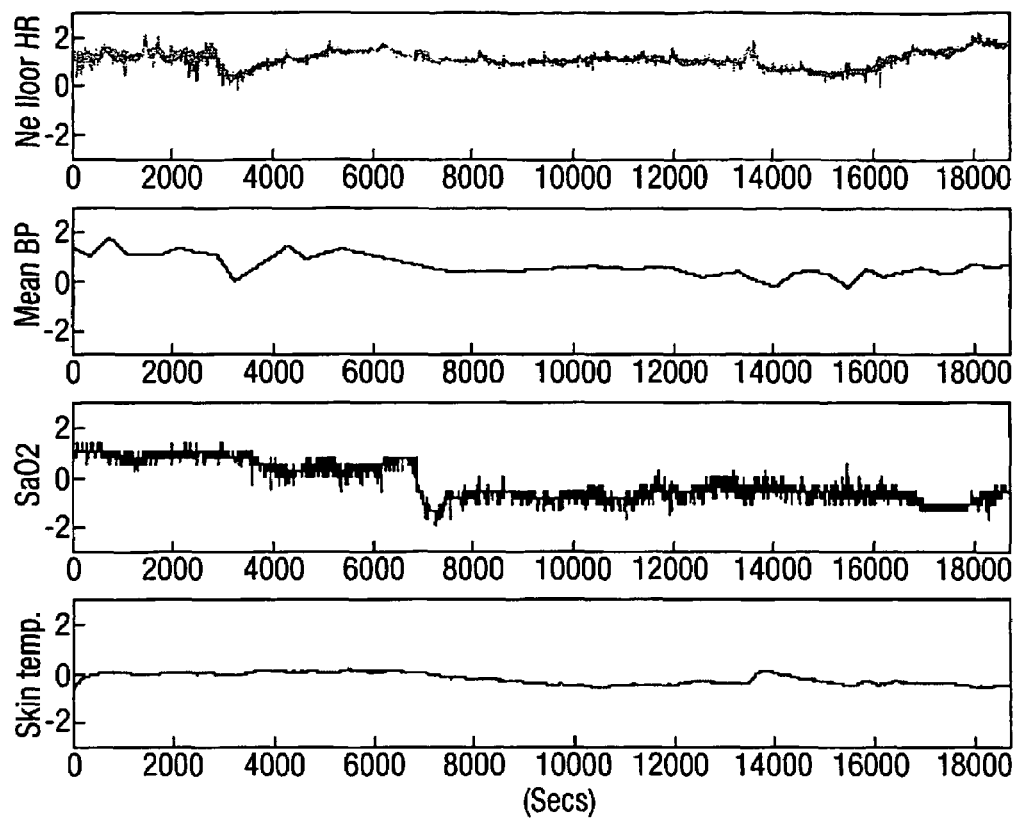
Figure 17C:
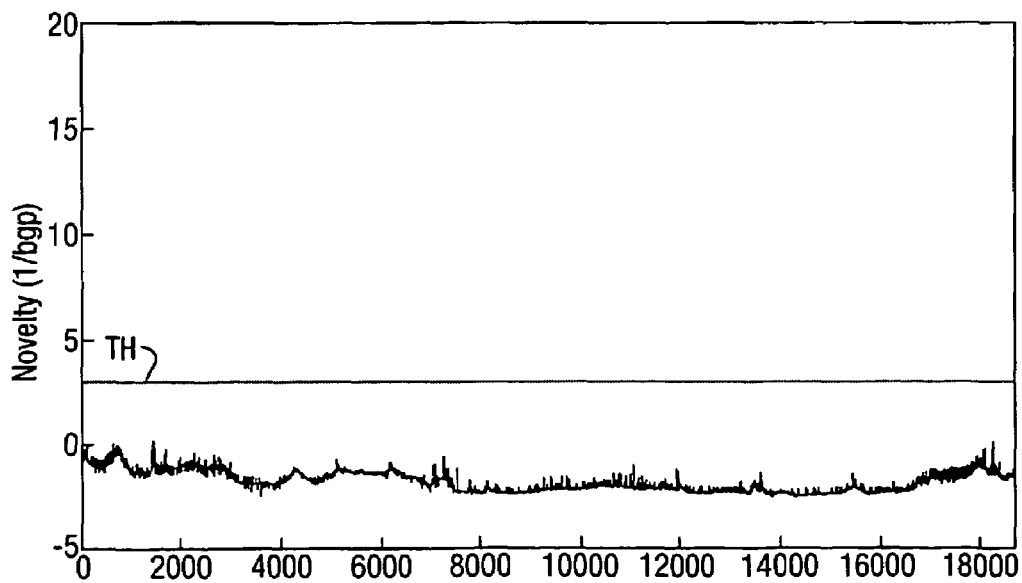
Figure 18B:
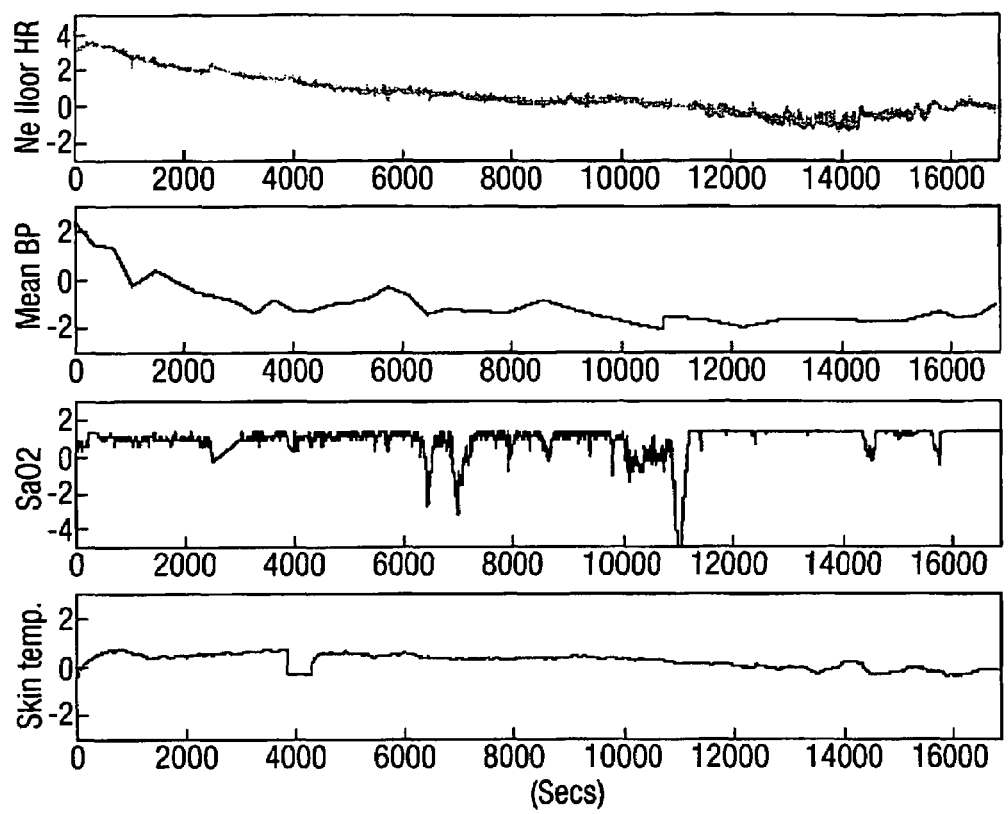
Figure 18C:
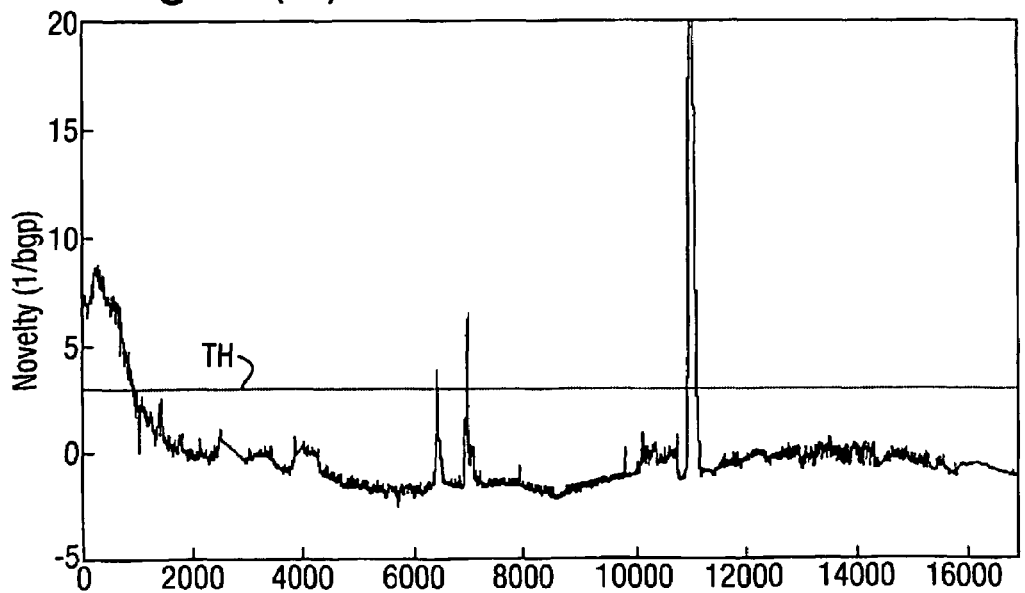

FIG. 17 illustrates the visualisation space, plots of four parameters, and plot of index of novelty against time for a patient whose condition remains normal. FIG. 18 illustrates in the same way the data from the patient of FIG. 16. It can be seen that the index of novelty decreases as the patient's condition improves at the beginning, but shows brief, sharp increases, particularly when the oxygen saturation drops on removal of the oxygen mask. FIGS. 19 and 20 are corresponding plots for the patient data shown in FIGS. 13 and 15, and it can be seen that the index of novelty and colour-coding follow the deterioration in the patient's condition.

We claim:

1. A method of displaying a graphical representation of a patient's condition as measured by n parameters, where n>3, comprising mapping data points represented by said n parameters from an n-dimensional measurement space into an m-dimensional visualization space, where m<n, using a dimensionality reduction mapping, and displaying the visualization space and the data points mapped into it, and wherein the displaying is adapted to the display of dynamically changing values of said parameters by means of the mapping being carried out by a trained artificial neural network, wherein said mapping maps each data point on receipt onto a novelty index constituting a one dimensional visualization space and the value of said novelty index is displayed against time, and wherein the novelty index of each point is based on its distance in the n-dimensional measurement space from a predefined set of points representing a normal condition for the patient.

2. A method according to claim 1, wherein the n parameters are selected from the group consisting of: a respiration measurement, an oxygen saturation measurement, blood pressure, skin temperature, S-T segment elevation/depression, heart rate, heart rate variability and respiration rate.

3. A method according to claim 2, wherein the respiration measurement is an impedance pneumography measurement.

4. A method according to claim 2, wherein the oxygen saturation measurement is a pulse oximetry measurement.

5. A method according to claim 1, further comprising normalizing the parameters prior to said mapping.

6. A method according to claim 5, wherein the normalization is by a zero mean, unit variance transformation.

7. A method according to claim 5, wherein the normalization is by an empirical transformation.

8. A method according to claim 1, wherein the dimensionality-reduction is a distance-preserving mapping.

9. A method according to claim 8, wherein the distance preserving mapping minimizes the difference in distance between pairs of points in the n-dimensional measurement space and the corresponding pairs of points in the m-dimensional visualization space.

10. A method according to claim 9, wherein the distance-preserving mapping is Sammon's mapping.

11. A method apparatus according to claim 1, wherein training data for the artificial neural network is provided by pre-clustering in the n-dimensional measurement space data points each comprising a set of said parameters, deriving the centers of the clusters, and using the centers of the clusters as the training data.

12. A method according to claim 11, wherein the data points are pre-clustered using the K-means method.

13. A method according to claim 1, wherein the artificial neural network is a Radial Basis Function (RBF) neural network.

14. A method according to claim 1, wherein the artificial neural network is trained with data comprising a set of said parameters from the patient.

15. A method according to claim 1, wherein the artificial neural network is trained with data comprising a plurality of sets of said parameters from a group of patients.

16. A method according to claim 1, further comprising generating an alarm responsive to said value of the novelty index exceeding a threshold.

17. A method according to claim 1, wherein the novelty index of each point is calculated by summing the distance in the n-dimensional measurement space between it and each of a set of prototype points representing the normal condition for the patient.

18. Apparatus for displaying a graphical representation of a patient's condition as measured by n parameters, where n>3, comprising a processor which maps data points represented by said n parameters from an n-dimensional measurement space into an m-dimensional visualization space, where m<n, using a dimensionality reduction mapping, and a display which displays the visualization space and the data points mapped into it, and which is adapted to the display of dynamically changing values of said parameters by means of the mapping being carried out by a trained artificial neural network, wherein said processor maps each data point on receipt onto a novelty index constituting a one dimensional visualization space and said display displays the value of said novelty index against time, and wherein the novelty index of each point is based on its distance in the n-dimensional measurement space from a predefined set of points representing a normal condition for the patient.

19. Apparatus according to claim 18, wherein the n parameters are selected from the group consisting of: a respiration measurement, an oxygen saturation measurement, blood pressure, skin temperature, S-T segment elevation/depression, heart rate, heart rate variability and respiration rate.

20. Apparatus according to claim 19, wherein the respiration measurement is an impedance pneumography measurement.

21. Apparatus according to claim 19, wherein the oxygen saturation measurement is a pulse oximetry measurement.

22. Apparatus according to claim 18, wherein said processor normalizes the parameters prior to said mapping.

23. Apparatus according to claim 22, wherein the processor normalizes the parameters using a zero mean, unit variance transformation.

24. Apparatus according to claim 22, wherein the processor normalizes the parameters using an empirical transformation.

25. Apparatus according to claim 18, wherein the dimensionality reduction is a distance-preserving mapping.

26. Apparatus according to claim 25, wherein the distance preserving mapping minimizes the difference in the distance between pairs of points in the n-dimensional measurement space and the corresponding pairs of points in the m-dimensional visualization space.

27. Apparatus according to claim 26, wherein the distance-preserving mapping is Sammon's mapping.

28. Apparatus according to claim 18, wherein the artificial neural network is a Radial Basis Function (RBF) neural network.

29. Apparatus according to claim 18, wherein the artificial neural network is trained with data comprising a plurality of sets of said parameters from the patient.

30. Apparatus according to claim 18, wherein the artificial neural network is trained with data comprising a plurality of sets of said parameters from a group of patients.

31. Apparatus according to claim 18, further comprising an alarm responsive to said value of the novelty index exceeding a threshold.

32. Apparatus according to claim 18, wherein the novelty index of each point is calculated by summing the distance in the n-dimensional measurement space between it and each of a set of prototype points representing the normal condition for the patient.

33. A patient condition monitor system comprising:
sensors for monitoring a condition of a patient; and
apparatus for displaying a graphical representation of a patient's condition as measured by n parameters based on data from the sensors, where n>3, the apparatus comprising a processor which maps data points represented by said n parameters from an n-dimensional measurement space into an m-dimensional visualization space, where m<n, using a dimensionality reduction mapping, and a display which displays the visualization space and the data points mapped into it, and which is adapted to the display of dynamically changing values of said parameters by means of the mapping being carried out by a trained artificial neural network, wherein said processor maps each data point on receipt onto a novelty index constituting a one dimensional visualization space and said display displays the value of said novelty index against time, and wherein the novelty index of each point is based on its distance in the n-dimensional measurement space from a predefined set of points representing a normal condition for the patient.

34. A computer program tangibly embodied on a computer readable storage medium and comprising instructions which, when executed by a computer system, perform a method of displaying a graphical representation of a patient's condition as measured by n parameters, where n>3, the method comprising mapping data points represented by said n parameters from an n-dimensional measurement space into an m-dimensional visualization space, where m<n, using a dimensionality reduction mapping, and displaying the visualization space and the data points mapped into it, and wherein the displaying is adapted to the display of dynamically changing values of said parameters by means of the mapping being carried out by a trained artificial neural network, wherein said mapping maps each data point on receipt onto a novelty index constituting a one dimensional visualization space and the value of said novelty index is displayed against time, and wherein the novelty index of each point is based on its distance in the n-dimensional measurement space from a predefined set of points representing a normal condition for the patient.

35. A computer readable storage medium on which a computer program is tangibly embodied, the computer program comprising instructions which, when executed by a computer system, perform a method of displaying a graphical representation of a patient's condition as measured by n parameters, where n>3, the method comprising mapping data points represented by said n parameters from an n-dimensional measurement space into an m-dimensional visualization space, where m<n, using a dimensionality reduction mapping, and displaying the visualization space and the data points mapped into it, and wherein the displaying is adapted to the display of dynamically changing values of said parameters by means of the mapping being carried out by a trained artificial neural network, wherein said mapping maps each data point on receipt onto a novelty index constituting a one dimensional visualization space and the value of said novelty index is displayed against time, and wherein the novelty index of each point is based on its distance in the n-dimensional measurement space from a predefined set of points representing a normal condition for the patient.

* * * * *